United States Patent
Thomas et al.

(10) Patent No.: US 9,913,764 B2
(45) Date of Patent: Mar. 13, 2018

(54) POST-BONDED GROOVED ELASTIC MATERIALS

(71) Applicant: Kimberly-Clark Worldwide, Inc., Neenah, WI (US)

(72) Inventors: Oomman P. Thomas, Alpharetta, GA (US); Bryan D. Haynes, Cumming, GA (US); Jerome J. Schwalen, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 45 days.

(21) Appl. No.: 14/132,091

(22) Filed: Dec. 18, 2013

(65) Prior Publication Data

US 2015/0164705 A1 Jun. 18, 2015

(51) Int. Cl.
*B32B 5/04* (2006.01)
*B32B 5/22* (2006.01)
(Continued)

(52) U.S. Cl.
CPC .... *A61F 13/4902* (2013.01); *A61F 13/15593* (2013.01); *Y10T 156/1044* (2015.01); *Y10T 428/24612* (2015.01)

(58) Field of Classification Search
CPC ......... B32B 27/06; B32B 27/08; B32B 27/12; B32B 27/32; B32B 27/302; B32B 27/045; B32B 5/022; B32B 5/04; B32B 7/045; B32B 25/04; B32B 5/26; A61F 13/47; A61F 13/49; A61F 13/4902; A61F 2013/51002; A61F 2013/51023; A61F 2013/51026; A61F 2013/51078; Y10T 428/24612; Y10T 428/31909; Y10T 428/24479; Y10T 428/24537
(Continued)

(56) References Cited

U.S. PATENT DOCUMENTS 3,338,992 A 8/1967 Kinney
3,341,394 A 9/1967 Kinney
(Continued)

FOREIGN PATENT DOCUMENTS

EP 1 194 102 B1 1/2005
WO WO 92/20250 A1 11/1992
(Continued)

OTHER PUBLICATIONS

Abstract of European Patent—EP0307871, Mar. 22, 1989, 1 page.
(Continued)

*Primary Examiner* — Joanna Pleszczynska
(74) *Attorney, Agent, or Firm* — Dority & Manning, P.A.

(57) ABSTRACT

An elastic nonwoven laminate that contains an elastic film laminated to one or more nonwoven facings is provided. The nonwoven facing contains a conventional polyolefin and can also contain a polyolefin-based plastomer. The laminate is activated by grooving to decouple the nonwoven facing from the elastic film. To reduce fiber-pull out that can result due to activation by grooving, the laminate can be post-bonded at room or elevated temperatures and a specific range of pressures to compact the fibers of the facing and minimize fiber pull-out/fuzziness while not sacrificing the softness, elasticity, and feel of the laminate.

10 Claims, 9 Drawing Sheets

(51) Int. Cl.
*B32B 5/26* (2006.01)
*B32B 7/04* (2006.01)
*B32B 27/06* (2006.01)
*B32B 27/08* (2006.01)
*B32B 27/12* (2006.01)
*B32B 27/32* (2006.01)
*A61F 13/49* (2006.01)
*A61F 13/15* (2006.01)

(58) Field of Classification Search
USPC ..... 428/172, 411.1, 500, 516, 521; 442/327, 442/328, 329, 394, 398; 604/367, 370, 604/372
See application file for complete search history.

(56) References Cited

U.S. PATENT DOCUMENTS

| | | | |
|---|---|---|---|
| 3,502,538 A | 3/1970 | Petersen | |
| 3,502,763 A | 3/1970 | Hartmann | |
| 3,542,615 A | 11/1970 | Dobo et al. | |
| 3,668,054 A | 6/1972 | Stump | |
| 3,692,618 A | 9/1972 | Dorschner et al. | |
| 3,694,867 A | 10/1972 | Stumpf | |
| 3,802,817 A | 4/1974 | Matsuki et al. | |
| 3,844,869 A | 10/1974 | Rust, Jr. | |
| 3,849,241 A | 11/1974 | Butin et al. | |
| 3,855,046 A | 12/1974 | Hansen et al. | |
| 3,939,033 A | 2/1976 | Grgach et al. | |
| 3,963,656 A | 6/1976 | Meisert et al. | |
| 4,041,203 A | 8/1977 | Brock et al. | |
| 4,259,399 A | 3/1981 | Hill | |
| 4,323,534 A | 4/1982 | DesMarais | |
| 4,340,563 A | 7/1982 | Appel et al. | |
| 4,374,888 A | 2/1983 | Bornslaeger | |
| 4,517,714 A | 5/1985 | Sneed et al. | |
| 4,663,220 A | 5/1987 | Wisneski et al. | |
| 4,704,116 A | 11/1987 | Enloe | |
| 4,766,029 A | 8/1988 | Brock et al. | |
| 4,789,592 A | 12/1988 | Taniguchi et al. | |
| 4,795,668 A | 1/1989 | Krueger et al. | |
| 4,834,738 A | 5/1989 | Kielpikowski et al. | |
| 4,886,512 A | 12/1989 | Damico et al. | |
| 4,937,299 A | 6/1990 | Ewen et al. | |
| 5,032,122 A | 7/1991 | Noel et al. | |
| 5,057,368 A | 10/1991 | Largman et al. | |
| 5,069,970 A | 12/1991 | Largman et al. | |
| 5,093,422 A | 3/1992 | Himes | |
| 5,096,532 A | 3/1992 | Neuwirth et al. | |
| 5,108,820 A | 4/1992 | Kaneko et al. | |
| 5,110,403 A | 5/1992 | Ehlert | |
| 5,162,074 A | 11/1992 | Hills | |
| 5,169,706 A | 12/1992 | Collier, IV et al. | |
| 5,213,881 A | 5/1993 | Timmons et al. | |
| 5,218,071 A | 6/1993 | Tsutsui et al. | |
| 5,226,992 A | 7/1993 | Morman | |
| 5,272,236 A | 12/1993 | Lai et al. | |
| 5,277,976 A | 1/1994 | Hogle et al. | |
| 5,278,272 A | 1/1994 | Lai et al. | |
| 5,304,599 A | 4/1994 | Himes | |
| 5,322,728 A | 6/1994 | Davey et al. | |
| 5,326,612 A | 7/1994 | Goulait | |
| 5,332,613 A | 7/1994 | Taylor et al. | |
| 5,336,552 A | 8/1994 | Strack et al. | |
| 5,382,400 A | 1/1995 | Pike et al. | |
| 5,399,219 A | 3/1995 | Roessler et al. | |
| 5,464,688 A | 11/1995 | Timmons et al. | |
| 5,466,410 A | 11/1995 | Hills | |
| 5,472,775 A | 12/1995 | Obijeski et al. | |
| 5,486,166 A | 1/1996 | Bishop et al. | |
| 5,490,846 A | 2/1996 | Ellis et al. | |
| 5,518,801 A | 5/1996 | Chappell et al. | |
| 5,539,056 A | 7/1996 | Yang et al. | |
| 5,540,796 A | 7/1996 | Fries | |
| 5,545,618 A | 8/1996 | Buckley et al. | |
| 5,558,659 A | 9/1996 | Sherrod et al. | |
| D375,844 S | 11/1996 | Edwards et al. | |
| 5,571,619 A | 11/1996 | McAlpin et al. | |
| 5,595,567 A | 1/1997 | King et al. | |
| 5,596,052 A | 1/1997 | Resconi et al. | |
| 5,605,961 A | 2/1997 | Lee et al. | |
| 5,614,281 A | 3/1997 | Jackson et al. | |
| 5,620,779 A | 4/1997 | Levy et al. | |
| 5,624,427 A | 4/1997 | Bergman et al. | |
| 5,649,916 A | 7/1997 | DiPalma et al. | |
| D390,708 S | 2/1998 | Brown | |
| 5,763,041 A | 6/1998 | Leak et al. | |
| 5,817,199 A | 10/1998 | Brennecke et al. | |
| 5,858,515 A | 1/1999 | Stokes et al. | |
| 5,888,607 A | 3/1999 | Seth et al. | |
| 5,932,497 A | 8/1999 | Morman et al. | |
| 5,962,112 A | 10/1999 | Haynes et al. | |
| 5,964,742 A | 10/1999 | McCormack et al. | |
| 5,997,981 A | 12/1999 | McCormack et al. | |
| 6,008,276 A | 12/1999 | Kalbe et al. | |
| 6,015,764 A | 1/2000 | McCormack et al. | |
| D428,267 S | 7/2000 | Romano, III et al. | |
| 6,090,325 A | 7/2000 | Wheat et al. | |
| 6,093,665 A | 7/2000 | Sayovitz et al. | |
| 6,110,158 A | 8/2000 | Kielpikowski | |
| 6,111,163 A | 8/2000 | McCormack et al. | |
| 6,200,669 B1 | 3/2001 | Marmon et al. | |
| 6,417,313 B2 | 7/2002 | Spyrou | |
| 6,461,457 B1 | 10/2002 | Taylor et al. | |
| 6,500,563 B1 | 12/2002 | Datta et al. | |
| 6,506,329 B1 | 1/2003 | Curro et al. | |
| 6,726,983 B2 | 4/2004 | Erdos et al. | |
| 6,846,376 B2 | 1/2005 | Kobayashi et al. | |
| 6,888,044 B2 | 5/2005 | Fell et al. | |
| 6,992,159 B2 | 1/2006 | Datta et al. | |
| 7,045,650 B2 | 5/2006 | Lawrey et al. | |
| 7,303,805 B2 | 12/2007 | Seth et al. | |
| 7,378,565 B2 | 5/2008 | Anderson et al. | |
| 8,231,595 B2 | 7/2012 | Turner et al. | |
| 8,604,129 B2 | 12/2013 | Thomas | |
| 2002/0105110 A1 | 8/2002 | Dobrin et al. | |
| 2004/0060112 A1 | 4/2004 | Fell et al. | |
| 2004/0110442 A1 | 6/2004 | Rhim et al. | |
| 2004/0241399 A1* | 12/2004 | Marmon | D04H 3/14 428/196 |
| 2006/0135728 A1 | 6/2006 | Peerlings et al. | |
| 2006/0151914 A1* | 7/2006 | Gerndt | B29C 55/065 264/288.4 |
| 2007/0049719 A1 | 3/2007 | Brauer et al. | |
| 2007/0141937 A1* | 6/2007 | Hendrix et al. | 442/170 |
| 2008/0155728 A1 | 7/2008 | Hafer et al. | |
| 2010/0168704 A1* | 7/2010 | Thomas et al. | 604/366 |
| 2011/0160687 A1 | 6/2011 | Welch et al. | |
| 2011/0250378 A1* | 10/2011 | Eaton et al. | 428/99 |
| 2012/0045626 A1* | 2/2012 | Inokuma | B32B 5/26 428/195.1 |
| 2012/0172516 A1 | 7/2012 | Wright et al. | |

FOREIGN PATENT DOCUMENTS

| | | |
|---|---|---|
| WO | WO 95/16425 A1 | 6/1995 |
| WO | WO 99/37839 A1 | 7/1999 |
| WO | WO 99/37841 A1 | 7/1999 |
| WO | WO 2006/071306 A1 | 7/2006 |
| WO | WO 2010001272 A2 | 1/2010 |
| WO | WO 2012/137084 A2 | 10/2012 |

OTHER PUBLICATIONS

Related U.S. Patent Form.
International Search Report and Written Opinion for PCT/IB2014/065875 dated Feb. 13, 2015, 14 pages.

* cited by examiner

POST-BONDED GROOVED ELASTIC MATERIALS

BACKGROUND OF THE INVENTION

Elastic laminates (e.g., multilayered materials having elastic properties) are used in a wide variety of absorbent articles. An elastic laminate generally has the ability to be stretched, and once the stretching force is removed, the material can retract and recover. In many applications, it is also desirable that the elastic laminates are soft and not sticky or tacky, as such laminates are often in contact with a user's skin. Moreover, in some instances, such elastic laminates are intended to be used more than one time. For example, the elastic laminates used for diaper ears that contain fastening mechanisms to secure the waistband of a diaper around a wearer may be unfastened and refastened multiple times to adjust the fit of the diaper or to check for insults in the diaper. Meanwhile, other elastic laminates can be included in an absorbent article in predetermined locations to optimize fit, make the article more comfortable to wear through improved fit, and/or improve the ability of the article to absorb liquids while preventing leakage through improved containment structures and gasketing.

Regardless of the particular absorbent article end use, elastic laminates can be made using various methods. In one method, a nonelastic component is joined to an elastic component while the elastic component is in a stretched condition so that when the elastic component is relaxed, the nonelastic component gathers between the locations where it is bonded to the elastic component. The resulting elastic laminate material is stretchable to the extent that the nonelastic component gathered between the bond locations allows the elastic component to elongate. It has been found that stretch bonded laminate materials tend to be fairly costly to manufacture and their inclusion in a product necessarily increases the cost of the end product to the consumer. It would therefore be desirable to provide efficient method for forming elastic materials having the desired level of softness and at a lower cost.

It is also known to laminate (or bond) a necked (neckable) material to an elastic sheet to produce a neck bonded laminate as described in U.S. Pat. No. 5,226,992 to Morman, et al. This process involves an elastic member being bonded to a non-elastic member while only the non-elastic member is extended in one direction (usually the machine direction) and necked in the transverse direction (usually the cross-machine direction) so as to reduce its dimension in the direction orthogonal to the extension. However, the production of such laminates is often not efficient, and the desired elastic properties may not be achieved, such as 200% elongation in the cross-machine direction, because elongation in the cross-machine direction is limited due to necking.

Another method of forming elastic laminates involves extrusion casting an elastic film onto a nonwoven facing or casting a film and adhesively bonding the film to at least one nonwoven facing. Then, the laminates can be subsequently incrementally stretched, such as by grooving, to provide machine direction or cross-machine direction stretch materials depending on the direction of the grooving. For example, machine direction grooving of the laminates allows cross-machine direction stretch by decoupling the facings from the elastic and cross-machine grooving of the laminates allows for machine direction stretch. However, in order to groove an elastic material to decouple the nonwoven facing from the elastic, the facing has often been based on a bonded carded web because the short length of the bonded carded web fibers and the decreased bonding area allows for the nonwoven facing to be grooved or striated while the elastic film remains continuous and undamaged. However, forming bonded carded webs and then grooving such webs is an expensive and time consuming, inefficient process requiring multiple steps. Further, the use of short fibers in the bonded carded web increases the amount of fiber pull out, which is not always desirable depending on the end-use application. On the other hand, it has been observed that the use of other nonwoven facings besides bonded carded webs, such as spunbond facings based on polypropylene with longer fibers and a larger percentage bond area cannot be grooved easily to provide elastic laminates that stretch and recover because of the materials used and the amount of post bonding, which also limits the softness of such materials compared to, for instance, polyethylene-based facings, which are also more cost effective. Further, grooving tends to loosen the fibers in such facings, which leads to difficulty in hook engagement and potentially increased fiber pull out, which can create challenges when utilizing these facings in absorbent article fastening systems. Also, the use of meltblown facings, although they may be easily grooved, is not ideal because of the loosely configured or fuzzy appearance and lack of integrity of the meltblown facings, as well as the potential disadvantages associated with fiber pull out in absorbent article applications.

As such, a need exists for a laminate utilizing meltblown or spunbond facings with sufficient elasticity, groovability, comfort, and softness that can also be used in absorbent article applications where minimal fiber pullout and durability are desired.

SUMMARY OF THE INVENTION

In accordance with one embodiment of the present invention, a method of forming an elastic laminate having a machine direction and a cross machine direction is disclosed. The method includes joining an elastic film with a nonwoven facing to form a laminate, where the nonwoven facing comprises a first polyolefin, the nonwoven facing is meltblown or spunbond, the elastic film is in an unstretched state. In addition, the method includes feeding the laminate through a first nip formed by a first roll and a second roll, where at least one of the rolls defines grooves, and where the laminate is fed in between the two rolls with sufficient nip pressure to groove the nonwoven facing such that the grooving decouples the nonwoven facing from the elastic film in the machine direction or the cross-machine direction. Moreover, the method includes feeding the laminate through a second nip formed by bond rolls at a bonding station to bond least an outer surface of the nonwoven facing, where the bonding occurs at a temperature ranging from about 65° F. to about 300° F. and at a pressure ranging from about 5 psi to about 100 psi.

In one embodiment, the first polyolefin includes polyethylene, polypropylene, or a combination thereof. In another embodiment, the laminate further includes a second polyolefin, where the second polyolefin comprises an elastomeric semi-crystalline polyolefin. The elastomeric semi-crystalline polyolefin can be an ethylene/α-olefin copolymer, propylene/α-olefin copolymer, or a combination thereof.

In yet another embodiment, the at least one of the bond rolls is patterned. The at least one bond roll can be patterned with raised bonding elements. Further, the at least one bond roll is patterned with a wire weave pattern. In addition, the pattern can cover from 10% to about 60% of the total surface area of the nonwoven facing.

In still another embodiment, the elastic film can be disposed between a first nonwoven facing and a second nonwoven facing. In another embodiment, the elastic nonwoven laminate can be grooved in the machine direction to provide cross-machine direction stretch to the elastic nonwoven laminate.

In an additional embodiment, a tab attached to the nonwoven facing can be elongated from about 50% to about 200% before becoming disengaged from the nonwoven facing. In one more embodiment, the elastic nonwoven laminate formed by the method of the present disclosure can have a percent elongation of at least about 200% in the cross machine direction.

In another embodiment, the elastic nonwoven laminate formed by the method of the present disclosure can include an elastic film, where the elastic film includes a core layer disposed between two skin layers, where the core layer is an elastic layer that includes a styrenic block copolymer, an ethylene/α-olefin copolymer, a propylene/α-olefin copolymer, or a combination thereof. In an additional embodiment, the elastic film can be disposed between a first nonwoven meltblown facing and a second nonwoven meltblown facing, where the elastic film comprises a core layer disposed between two skin layers, and where the core layer is a strength layer and the two skin layers are elastic layers.

In accordance with another embodiment of the present invention, an elastic laminate having a machine direction and a cross machine direction is disclosed. The elastic nonwoven laminate includes an unstretched elastic film positioned adjacent a nonwoven facing. The nonwoven facing includes a first polyolefin, and the nonwoven facing is meltblown or spunbond. Further, the nonwoven facing is grooved in the machine direction or cross-machine direction, and at least an outer surface of the nonwoven facing is bonded. In addition, the elastic nonwoven laminate has a percent elongation of at least about 200% in the cross machine direction.

In one particular embodiment, the first polyolefin includes polyethylene, polypropylene, or a combination thereof. In still another embodiment, the nonwoven facing further includes a second polyolefin, wherein the second polyolefin comprises an elastomeric semi-crystalline polyolefin. The elastomeric semi-crystalline polyolefin can be an ethylene/α-olefin copolymer, propylene/α-olefin copolymer, or a combination thereof. In one embodiment, the first polyolefin can be present in an amount ranging from about 50 wt. % to about 99 wt. % and the second polyolefin can be present in an amount ranging from about 0.5 wt. % to about 60 wt. %, based on the total weight of the nonwoven facing.

In one more embodiment, the outer surface of the nonwoven facing can be bonded in a pattern, such as a wire weave pattern.

In yet another embodiment, the elastic film can be disposed between a first nonwoven facing and a second nonwoven facing.

In still another embodiment, the elastic film can include a core layer disposed between two skin layers, where the core layer is an elastic layer that includes a styrenic block copolymer, an ethylene/α-olefin copolymer, a propylene/α-olefin copolymer, or a combination thereof.

In an additional embodiment, the elastic film can be disposed between a first nonwoven meltblown facing and a second nonwoven meltblown facing, where the elastic film includes a core layer disposed between two skin layers, where the core layer is a strength layer, and where the two skin layers are elastic layers.

In one more embodiment, a tab attached to the nonwoven facing can be elongated from about 50% to about 200% before becoming disengaged from the nonwoven facing. Further, the elastic nonwoven laminate can have a percent elongation of at least about 200% in the cross-machine direction.

In yet another embodiment, the elastic nonwoven laminate can further a frangible layer. In an additional embodiment, the present invention contemplates an absorbent article comprising the elastic nonwoven laminate as discussed above. Further, the absorbent article can include an ear or fastening component that includes the elastic nonwoven laminate as described above. In another embodiment, a waist band, leg band, or both can include the elastic nonwoven laminate as described above.

Other features and aspects of the present invention are described in more detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
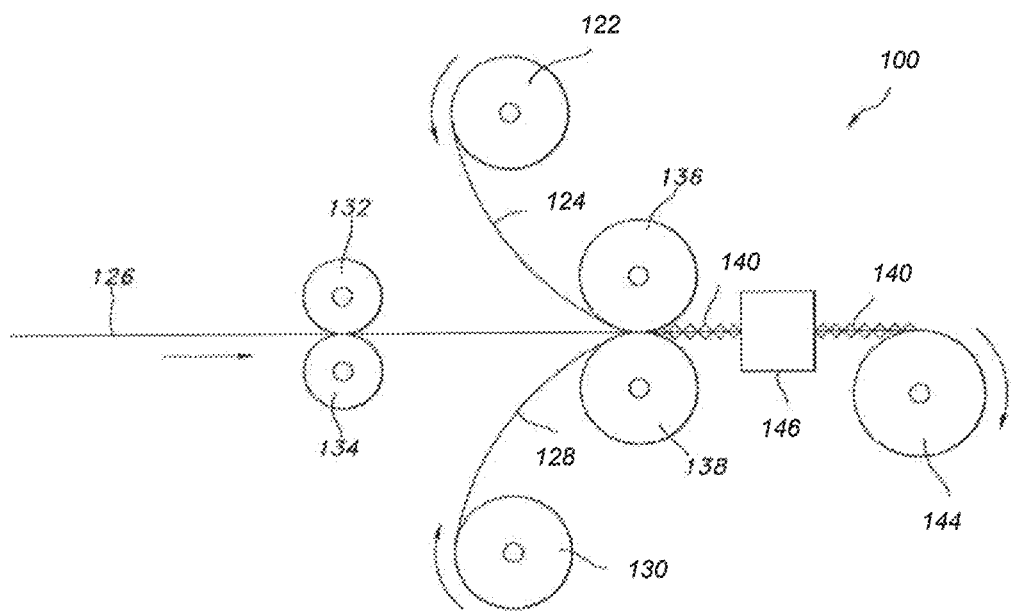
FIG. 1 schematically illustrates a method for forming a composite according to one embodiment of the present invention.

Repeat use of reference characters in the present specification and drawings is intended to represent the same or analogous features or elements of the invention.

DETAILED DESCRIPTION OF REPRESENTATIVE EMBODIMENTS

Definitions

As used herein, the terms "machine direction" or "MD" generally refers to the direction in which a material is produced. The term "cross-machine direction" or "CD" refers to the direction perpendicular to the machine direction.

As used herein the term "nonwoven web" generally refers to a web having a structure of individual fibers or threads which are interlaid, but not in an identifiable manner as in a knitted fabric. Examples of suitable nonwoven fabrics or webs include, but are not limited to, meltblown webs, spunbond webs, bonded carded webs, airlaid webs, coform webs, hydraulically entangled webs, and so forth.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 3,338,992 to Kinney, U.S. Pat. No. 3,341,394 to Kinney, U.S. Pat. No. 3,502,538 to Levy, U.S. Pat. No. 3,502,763 to Hartman, U.S. Pat. No. 3,542,615 to Dobo, et al., U.S. Pat. No. 3,692,618 to Dorschner, et al., U.S. Pat. No. 3,802,817 to Matsuki, et al., U.S. Pat. No. 4,340,563 to Appel, et al., and U.S. Pat. No. 5,382,400 to Pike et al., which are incorporated herein in their entirety by reference thereto for all purposes. Spunbond fibers are generally not tacky when they are deposited onto a collecting surface. As such, the fibers may be bonded together after deposition onto a collecting surface in order to integrate the fibers. Spunbond fibers may sometimes have diameters less than about 40 microns, and are often between about 5 to about 20 microns.

As used herein, the term "bonded carded web" refers to webs made from staple fibers which are sent through a combing or carding unit, which breaks apart and aligns the staple fibers in the machine direction to form a generally machine direction-oriented fibrous nonwoven web. Such fibers are usually purchased in bales which are placed in a picker or fiberizer which separates the fibers prior to the carding unit. Once the web is formed, it is then bonded by one or more of several known bonding methods.

As used herein the terms "extensible" or "extensibility" generally refers to a material that stretches or extends in the direction of an applied force by at least about 25%, in some embodiments about 50%, and in some embodiments, at least about 75% of its relaxed length or width. An extensible material does not necessarily have recovery properties. For example, an elastomeric material is an extensible material having recovery properties, while a necked meltblown web may be extensible, but not have recovery properties, and thus, is considered an extensible, non-elastic material.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein, the term "necked material" refers to any material which has been narrowed in at least one dimension by application of a tensioning force.

As used herein, the term "thermal point bonding" generally refers to a process performed, for example, by passing a material between a patterned roll (e.g., calender roll) and another roll (e.g., anvil roll), which may or may not be patterned. One or both of the rolls are typically heated.

As used herein, the term "ultrasonic bonding" generally refers to a process performed, for example, by passing a material between a sonic horn and a patterned roll (e.g., anvil roll). For instance, ultrasonic bonding through the use of a stationary horn and a rotating patterned anvil roll is described in U.S. Pat. No. 3,844,869 to Rust Jr., U.S. Pat. No. 3,939,033 to Grgach, et al., and U.S. Pat. No. 4,259,399 to Hill, which are incorporated herein in their entirety by reference thereto for all purposes. Moreover, ultrasonic bonding through the use of a rotary horn with a rotating patterned anvil roll is described in U.S. Pat. No. 5,096,532 to Neuwirth et al., U.S. Pat. No. 5,110,403 to Ehlert, and U.S. Pat. No. 5,817,199 to Brennecke, et al., which are incorporated herein in their entirety by reference thereto for all purposes. Of course, any other ultrasonic bonding technique may also be used in the present invention.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to an elastic nonwoven laminate that contains an elastic film laminated to one or more nonwoven facings. The nonwoven facing can include a conventional polyolefin which can, in some embodiments, be combined with a polyolefin-based plastomer. Further, the nonwoven facing can be spunbond or meltblown. The laminate can be activated by grooving and then can be post-bonded. By activation, it is meant that the laminate's elasticity, attributed to the elastic film, is unlocked, such as by breaking portions of the nonwoven facing. The present inventors have found that by selectively controlling certain parameters of the lamination process, such as film content, nonwoven facing content, bonding pattern, bonding conditions, etc., a desired level of compaction to prevent the fiber pull-out typically seen in groove-activated spunbond or meltblown webs can be achieved without sacrificing the elasticity, softness, loftiness, hand feel, and/or aesthetic appeal of the resulting laminate. Thus, a spunbond or meltblown elastic nonwoven laminate can be produced that can be reusable, such as in fastening/unfastening applications, due to the reduced occurrence of fiber pull-out, which also minimizes the "fuzziness" of the laminate despite utilizing grooving to activate the laminates instead of other activation methods, such as heat activation. As such, the elastic nonwoven laminate of the present invention can be used instead of bonded carded web-based elastic laminates. Further, Applicants have found that an improved bond can be formed between the nonwoven facings and the elastic film of the elastic nonwoven laminates of the present invention compared to bonded carded web elastic laminates, which are more loosely configured or fuzzier.

In this regard, various embodiments of the present invention will now be described in more detail.

I. Elastic Film

The elastic film component of the elastic nonwoven laminate of the present invention is formed from one or more layers of polymers that are melt-processable, i.e., thermoplastic. For instance, in one particular embodiment, the elastic film can be a monolayer film. If the film is a monolayer, any of the polymers discussed below in reference to the core layer or skin layers is contemplated by the present invention. In other embodiments, the elastic film can include two, three, four, five, six, or seven layers. For example, a three-layer film that comprises a core layer sandwiched between two skin layers is contemplated. However, it is to be understood that any number of layers can be present, where the one or more layers are formed from the same or different materials. Various configurations for the arrangement of the elastic film in conjunction with the nonwoven facing are discussed below in section III.

a. Core Layer

The core layer of the elastic film of the elastic nonwoven laminate of the present invention can provide the laminate with the desired elasticity. Any of a variety of thermoplastic elastomeric or plastomeric polymers may generally be employed in the core layer of the elastic film of the elastic nonwoven laminate of the present invention. Such polymers include elastomeric polyesters, elastomeric polyurethanes, elastomeric polyamides, elastomeric copolymers, elastomeric polyolefins, and so forth. In one embodiment, for instance, a substantially amorphous block copolymer may be employed that contains blocks of a monoalkenyl arene and a saturated conjugated diene. Such block copolymers are particularly useful in the present invention due to their high degree of elasticity.

The monoalkenyl arene block(s) may include styrene and its analogues and homologues, such as o-methyl styrene; p-methyl styrene; p-tert-butyl styrene; 1,3 dimethyl styrene p-methyl styrene; etc., as well as other monoalkenyl polycyclic aromatic compounds, such as vinyl naphthalene; vinyl anthrycene; and so forth. Preferred monoalkenyl arenes are styrene and p-methyl styrene. The conjugated diene block(s) may include homopolymers of conjugated diene monomers, copolymers of two or more conjugated dienes, and copolymers of one or more of the dienes with another monomer in which the blocks are predominantly conjugated diene units. Preferably, the conjugated dienes contain from 4 to 8 carbon atoms, such as 1,3 butadiene (butadiene); 2-methyl-1,3 butadiene; isoprene; 2,3 dimethyl-1,3 butadiene; 1,3 pentadiene (piperylene); 1,3 hexadiene; and so forth. The amount of monoalkenyl arene (e.g., polystyrene) blocks may vary, but typically constitute from about 8 wt. % to about 55 wt. %, in some embodiments from about 10 wt. % to about 35 wt. %, and in some embodiments from about 15 wt. % to about 25 wt. % of the copolymer. Suitable block copolymers may contain monoalkenyl arene endblocks having a number average molecular weight from about 5,000 to about 35,000 and saturated conjugated diene midblocks having a number average molecular weight from about 20,000 to about 170,000. The total number average molecular weight of the block polymer may be from about 30,000 to about 250,000.

Particularly suitable thermoplastic elastomeric copolymers are available from Kraton Polymers LLC of Houston, Tex. under the trade name KRATON®. KRATON® polymers include styrene-diene block copolymers, such as styrene-butadiene, styrene-isoprene, styrene-butadiene-styrene, styrene-isoprene-styrene, and styrene-isoprene/butadiene-styrene. KRATON® polymers also include styrene-olefin block copolymers formed by selective hydrogenation of styrene-diene block copolymers. Examples of such styrene-olefin block copolymers include styrene-(ethylene-butylene), styrene-(ethylene-propylene), styrene-(ethylene-butylene)-styrene, styrene-(ethylene-propylene)-styrene, styrene-(ethylene-butylene)-styrene-(ethylene-butylene), styrene-(ethylene-propylene)-styrene-(ethylene-propylene), and styrene-ethylene-(ethylene-propylene)-styrene. These styrenic block copolymers may have a linear, radial or star-shaped molecular configuration. Specific KRATON™ block copolymers include those sold under the brand names D 1102, D 1171, G 1652, G 1657, G 1730, MD 6673, and MD 6973. Various suitable styrenic block copolymers are described in U.S. Pat. No. 4,323,534 to DesMarais, U.S. Pat. No. 4,663,220 to Wisneski, et al., U.S. Pat. No. 4,834,738 to Kielpikowski et al., U.S. Pat. No. 5,093,422 to Himes, and U.S. Pat. No. 5,304,599 to Himes, as well as U.S. Patent Application Publication Nos. 2012/0172214 to Thomas and 2012/0172516 to Wright, et al., which are hereby incorporated in their entirety by reference thereto for all purposes. Other commercially available block copolymers include the S-EP-S elastomeric copolymers available from Kuraray Company, Ltd. of Okayama. Japan, under the trade designation SEPTON™. Still other suitable copolymers include S-I-S and S-B-S elastomeric copolymers, which are available from Dexco Polymers of Houston, Tex. or TSRC Company of Taiwan under the trade designation VECTOR™. Also suitable are polymers composed of an A-B-A-B tetrablock copolymer, such as discussed in U.S. Pat. No. 5,332,613 to Taylor, et al., which is incorporated herein in its entirety by reference thereto for all purposes. An example of such a tetrablock copolymer is a styrene-poly (ethylene-propylene)-styrene-poly(ethylene-propylene) ("S-EP-S-EP") block copolymer.

In one particular embodiment, the core layer of the elastic film of the present invention can include multiple styrenic block copolymers. For instance, the elastic film can include a styrene-butadiene-styrene copolymer and a styrene-isoprene/butadiene-styrene copolymer. The styrene-butadiene-styrene copolymer can be present in an amount ranging from about 5 wt. % to about 60 wt. %, such as from about 10 wt. % to about 55 wt. %, such as from about 15 wt. % to about 50 wt. % based on the total weight of the core layer. Meanwhile, the styrene-isoprene/butadiene-styrene copolymer can be present in an amount ranging from about 30 wt. % to about 75 wt. %, such as from about 35 wt. % to about 70 wt. %, such as from about 40 wt. % to about 65 wt. % based on the total weight of the core layer.

Of course, other thermoplastic elastomeric polymers may also be used to form the film, either alone or in conjunction with the block copolymers. Semi-crystalline polyolefins, for example, may be employed that have or are capable of exhibiting a substantially regular structure. Exemplary semi-crystalline polyolefins include polyethylene, polypropylene, blends and copolymers thereof. In one particular embodiment, a polyethylene is employed that is a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Particularly suitable polyethylene copolymers are those that are "linear" or "substantially linear." The term "substantially linear" means that, in addition to the short chain branches attributable to comonomer incorporation, the ethylene polymer also contains long chain branches in the polymer backbone. "Long chain branching" refers to a chain length of at least 6 carbons. Each long chain branch may have the same comonomer distribution as the polymer backbone and be as long as the polymer backbone to which it is attached. Preferred substantially linear polymers are substituted with from 0.01 long chain branch per 1000 carbons to 1 long chain branch per 1000 carbons, and in some embodiments, from 0.05 long chain branch per 1000 carbons to 1 long chain branch per 1000 carbons. In contrast to the term "substantially linear", the term "linear" means that the polymer lacks measurable or demonstrable long chain branches. That is, the polymer is substituted with an average of less than 0.01 long chain branch per 1000 carbons.

The density of a linear ethylene/α-olefin copolymer is a function of both the length and amount of the α-olefin. That is, the greater the length of the α-olefin and the greater the amount of α-olefin present, the lower the density of the copolymer. Although not necessarily required, linear polyethylene "plastomers" are particularly desirable in that the content of α-olefin short chain branching content is such that the ethylene copolymer exhibits both plastic and elastomeric characteristics—i.e., a "plastomer." Because polymerization with α-olefin comonomers decreases crystallinity and density, the resulting plastomer normally has a density lower than that of a polyethylene thermoplastic polymer (e.g., LLDPE), which typically has a density (specific gravity) of from about 0.90 grams per cubic centimeter (g/cm$^3$) to about 0.94 g/cm$^3$, but approaching and/or overlapping that of an elastomer, which typically has a density of from about 0.85 g/cm$^3$ to about 0.90 g/cm$^3$, preferably from 0.86 to 0.89. For example, the density of the polyethylene plastomer may be 0.91 g/cm$^3$ or less, in some embodiments from about 0.85 g/cm$^3$ to about 0.90 g/cm$^3$, in some embodiments, from 0.85 g/cm$^3$ to 0.88 g/cm$^3$, and in some embodiments, from 0.85 g/cm$^3$ to 0.87 g/cm$^3$. Despite having a density similar to elastomers, plastomers generally exhibit a higher degree of crystallinity, are relatively non-tacky, and may be formed into pellets that are non-adhesive-like and relatively free flowing.

Preferred polyethylenes for use in the present invention are ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. An additional suitable polyethylene-based plastomer is an olefin block copolymer available from Dow Chemical Company of Midland, Mich. under the trade designation INFUSE™, which is an elastomeric copolymer of polyethylene. Still other suitable ethylene polymers are low density polyethylenes (LDPE), linear low density polyethylenes (LLDPE) or ultralow linear density polyethylenes (ULDPE), such as those available from The Dow Chemical Company under the designations ASPUN™ (LLDPE), DOWLEX™ (LLDPE) and ATTANET™ (ULDPE). Other suitable ethylene polymers are described in U.S. Pat. No. 4,937,299 to Ewen, et al., U.S. Pat. No. 5,218,071 to Tsutsui et al., U.S. Pat. No. 5,272,236 to Lai, et al., and U.S. Pat. No. 5,278,272 to Lai, et al., which are incorporated herein in their entirety by reference thereto for all purposes.

Of course, the present invention is by no means limited to the use of ethylene polymers. For instance, propylene plastomers may also be suitable for use in the film. Suitable plastomeric propylene polymers may include, for instance, copolymers or terpolymers of propylene, copolymers of propylene with an α-olefin (e.g., $C_3$-$C_{20}$), such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, and in some embodiments, from about 2 wt. % to about 10 wt. %. Preferably, the density of the polypropylene (e.g., propylene/α-olefin copolymer) may be 0.91 g/cm$^3$ or less, in some embodiments, from 0.85 g/cm$^3$ to 0.88 g/cm$^3$, and in some embodiments, from 0.85 g/cm$^3$ to 0.87 g/cm$^3$. Suitable propylene polymers are commercially available under the designations VISTAMAXX™ (e.g., 6102), a propylene-based elastomer from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 5,539,056 to Yang, et al., U.S. Pat. No. 5,596,052 to Resconi, et al., and U.S. Pat. No. 6,500,563 to Datta, et al., which are incorporated herein in their entirety by reference thereto for all purposes.

Any of a variety of known techniques may generally be employed to form the semi-crystalline polyolefins. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,272,236 to Lai et al., U.S. Pat. No. 5,322,728 to Davis et at, U.S. Pat. No. 5,472,775 to Objjeski et al., U.S. Pat. No. 5,571,619 to McAlpin et al., and U.S. Pat. No. 6,090,325 to Wheat, et al., which are incorporated herein in their entirety by reference thereto for all purposes. Examples of metallocene catalysts include bis(n-butylcyclopentadienyl)titanium dichloride, bis(n-butylcyclopentadienyl)zirconium dichloride, bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

The melt flow index (MI) of the semi-crystalline polyolefins may generally vary, but is typically in the range of about 0.1 grams per 10 minutes to about 100 grams per 10 minutes, in some embodiments from about 0.5 grams per 10 minutes to about 30 grams per 10 minutes, and in some embodiments, about 1 to about 10 grams per 10 minutes, determined at 190° C. The melt flow index is the weight of the polymer (in grams) that may be forced through an extrusion rheometer orifice (0.0825-inch diameter) when subjected to a force of 5000 grams in 10 minutes at 190° C., and may be determined in accordance with ASTM Test Method D1238-E.

The present invention also contemplates the use of thermoplastic polyurethanes as a component of the core layer of the film. Thermoplastic polyurethanes are generally synthesized from a polyol, organic diisocyanate, and optionally a chain extender. The synthesis of such melt-processable polyurethane elastomers may proceed either stepwise (e.g., prepolymer dispensing process) or by simultaneous reaction of all components in a single stage (e.g., one-shot dispensing process) as is known in the art and described in more detail in U.S. Pat. No. 3,963,656 to Meisert, et al., U.S. Pat. No. 5,605,961 to Lee, et al., U.S. Pat. No. 6,008,276 to Kalbe, et al., U.S. Pat. No. 6,417,313 to Kirchmeyer, et al., and U.S. Pat. No. 7,045,650 to Lawrey, et al., as well as U.S. Patent Application Publication Nos. 2006/0135728 to Peerlings, et al. and 2007/0049719 to Brauer, et al., all of which are incorporated herein in their entirety by reference thereto for all purposes.

Thermoplastic polyurethanes can typically have a melting point of from about 75° C. to about 250° C., in some embodiments from about 100° C. to about 240° C., and in some embodiments, from about 120° C. to about 220° C. The glass transition temperature ("$T_g$") of the thermoplastic polyurethane may be relatively low, such as from about −150° C. to about 0° C., in some embodiments from about −100° C. to about −10° C., and in some embodiments, from about −85° C. to about −20° C. The melting temperature and glass transition temperature may be determined using differential scanning calorimetry ("DSC") in accordance with ASTM D-3417. Examples of such thermoplastic polyurethanes are available under the designation DESMOPAN™ from Bayer MaterialScience and under the designation ESTANE™ from Lubrizol. DESMOPAN™ DP 9370A, for instance, is an aromatic polyether-based polyurethane formed from poly(tetramethylene ether glycol) and 4,4-methylenebis(phenylisocyanate) ("MDI") and has a glass transition temperature of about −70° C. and a melting temperature of from about 188° C. to about 199° C. ESTANE™ 58245 is likewise an aromatic polyether-based polyurethane having a glass transition temperature of about −37° C. and a melting temperature of from about 135° C. to about 159° C.

The present invention also contemplates the use of thermoplastic ester elastomers and thermoplastic ether elastomers. Of course, besides elastomeric polymers, generally inelastic thermoplastic polymers may also be used so long as they do not adversely affect the elasticity of the laminate. For example, the thermoplastic composition of the core layer may contain other polyolefins (e.g., polypropylene, polyethylene, etc.). In one embodiment, the thermoplastic composition may contain an additional propylene polymer, such as homopolypropylene or a copolymer of propylene. The additional propylene polymer may, for instance, be formed from a substantially isotactic polypropylene homopolymer or a copolymer containing equal to or less than about 10 wt. % of other monomer, i.e., at least about 90% by weight propylene. Such a polypropylene may be present in the form of a graft, random, or block copolymer and may be predominantly crystalline in that it has a sharp melting point above about 110° C., in some embodiments about above 115° C., and in some embodiments, above about 130° C. Examples of such additional polypropylenes are described in U.S. Pat. No. 6,992,159 to Datta, et al., which is incorporated herein in its entirety by reference thereto for all purposes.

b. Skin Layers

As discussed above, it is to be understood that the elastic film component of the elastic nonwoven laminate of the present invention may be monolayered or multilayered. Multilayered films may be prepared by co-extrusion or any other conventional layering technique. When employed, the multilayered film can typically contain at least one thermoplastic skin layer and at least one core layer (as discussed above). For instance, the thermoplastic skin layer(s) may be employed to provide strength and integrity to the resulting multilayered film via improved tensile strength, while the elastic core layer may be employed to provide elasticity to the multilayered film. However, it is also to be understood that, in some embodiments, the skin layer(s) can include the elastic components that are discussed above in reference to the core layer, and the core layer can include the strength and integrity components discussed herein in reference to the skin layer(s).

In one particular embodiment of the present invention, the film includes at least one elastic core layer positioned between at least two thermoplastic skin layers. In such embodiments, the core layer can provide the desired degree of elasticity to the multilayered film. To impart the desired elastic properties to the film, elastomers can constitute about 55 wt. % or more, in some embodiments about 60 wt. % or more, and in some embodiments, from about 65 wt. % to about 100 wt. % of the polymer content of the elastomeric composition used to form the core layer. In fact, in certain embodiments, the core layer may be generally free of polymers that are inelastic. For example, such inelastic polymers may constitute about 15 wt. % or less, in some embodiments about 10 wt. % or less, and in some embodiments, about 5 wt. % or less of the polymer content of the elastomeric composition.

Meanwhile, although the skin layers may possess some degree of elasticity and may, in some embodiments, be formed from any of the materials discussed above, in some embodiments, such layers may be formed from a thermoplastic composition that is less elastic than the elastic layer(s) to ensure that the strength of the film is sufficiently enhanced. For example, one or more elastic layers may be formed primarily from substantially amorphous elastomers (e.g., styrene-olefin copolymers) and one or more thermoplastic layers may be formed from polyolefin plastomers (e.g., single-site catalyzed ethylene or propylene copolymers), which are described in more detail above. Although possessing some elasticity, such polyolefins are generally less elastic than substantially amorphous elastomers. Of course, the thermoplastic layer(s) may contain generally inelastic polymers, such as conventional polyolefins, (e.g., polyethylene), low density polyethylene (LDPE), Ziegler-Natta catalyzed linear low density polyethylene (LLDPE), etc.), ultra low density polyethylene (ULDPE), polypropylene, polybutylene, etc.; polytetrafluoroethylene; polyesters, e.g., polyethylene terephthalate (PET), etc.; polyvinyl acetate; polyvinyl chloride acetate; polyvinyl butyral; acrylic resins, e.g., polyacrylate, polymethylacrylate, polymethylmethacrylate, etc.; polyamides, e.g., nylon; polyvinyl chloride; polyvinylidene chloride; polystyrene; polyvinyl alcohol; polyurethanes; polylactic acid; copolymers and mixtures thereof; and so forth. For instance, the skin layers can be formed from an LLDPE available from Dow Chemical Co. of Midland, Mich., such as DOWLEX™ 2517 or DOWLEX™ 2047, or a combination thereof, or Westlake Chemical Corp. of Houston, Tex. In certain embodiments, polyolefins (e.g., conventional and/or plastomers) can be employed and constitute about 55 wt. % or more, in some embodiments about 60 wt. % or more, and in some embodiments, from about 65 wt. % to 100 wt. % of the polymer content of the thermoplastic composition used to form the skin layers. Regardless of the components used in forming the skin layers, the skin layers generally have an elongation at break that is greater than about 300%.

The weight percentages of the core and skin layers in the elastic film can be generally selected so as to achieve an appropriate balance between film elasticity and strength. For instance, the thickness of the core layer can typically range from about 20 to about 200 micrometers, in some embodiments from about 25 to about 175 micrometers, and in some embodiments, from about 30 to about 150 micrometers. The core layer may also constitute from about 50 wt. % to about 99 wt. % of the total weight of the film, in some embodiments from about 70 wt. % to about 98 wt. % of the total weight of the film, and in some embodiments from about 85% to about 97% of the total weight of the film. On the other hand, the thickness of the one or more skin layers can typically range from about 0.5 to about 20 micrometers, in some embodiments from about 1 to about 15 micrometers, and in some embodiments, from about 2 to about 12 micrometers. The skin layer(s) may also constitute from about 1 wt. % to about 50 wt. % of the total weight of the film, in some embodiments from about 2 wt. % to about 20 wt. % of the total weight of the film, and in some embodiments from about 3 wt. % to about 15 wt. %, and in some embodiments from about 5 wt. % to about 10 wt. % of the total weight of the film. In one particular embodiment, an elastic core layer can be sandwiched between two thermoplastic skin layers, where the thickness of each of the skin layers is equal. For example, in one embodiment, the film can include a core layer that constitutes 96% of the total weight of the film, while the skin layers each constitute 2% of the total weight of the film. The film may also have a total thickness of from about 20 to about 250 micrometers, in some embodiments, from about 25 to about 225 micrometers, and in some embodiments, from about 30 to about 200 micrometers.

c. Other Film Components

Further, the various layers of the film of the present invention may also contain other components as are known in the art. In one embodiment, for example, one or more of the film layers can include a filler. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. No. 5,932,497 to Morman, et al., U.S. Pat. Nos. 5,997, 981, 6,015,764, and 6,111,163 to McCormack, et al., and U.S. Pat. No. 6,461,457 to Taylor, et al., which are incorporated herein in their entirety by reference thereto for all purposes. Examples of suitable fillers include, but are not limited to, calcium carbonate, various kinds of clay, silica, alumina, barium carbonate, sodium carbonate, magnesium carbonate, talc, barium sulfate, magnesium sulfate, aluminum sulfate, titanium dioxide (e.g., SCC 11692 concentrated titanium dioxide), zeolites, cellulose-type powders, kaolin, mica, carbon, calcium oxide, magnesium oxide, aluminum hydroxide, pulp powder, wood powder, cellulose derivatives, chitin and chitin derivatives. In certain cases, the filler content of the film may range from about 0.1 wt. % to about 10 wt. %, in some embodiments, from about 0.5 wt. % to about 7.5 wt. %, and in some embodiments, from about 1 wt. % to about 5 wt. % of the film based on the total weight of the film.

Other additives may also be incorporated into the film, such as melt stabilizers, crosslinking catalysts, pro-rad crosslinking additives, processing stabilizers, heat stabilizers, light stabilizers, antioxidants, heat aging stabilizers, whitening agents, antiblocking agents, bonding agents, tackifiers, viscosity modifiers, etc. Examples of suitable tackifier resins may include, for instance, hydrogenated hydrocarbon resins. REGALREZ™ hydrocarbon resins are examples of such hydrogenated hydrocarbon resins, and are available from Eastman Chemical. Other tackifiers are available from ExxonMobil under the ESCOREZ™ designation. Viscosity modifiers may also be employed, such as polyethylene wax (e.g., EPOLENE™ C-10 from Eastman Chemical). Phosphite stabilizers (e.g., IRGAFOS™ 168 available from Ciba Specialty Chemicals of Tarrytown, N.Y. and DOVERPHOS™ available from Dover Chemical Corp. of Dover, Ohio) are exemplary melt stabilizers. In addition, hindered amine stabilizers (e.g., CHIMASSORB™ available from Ciba Specialty Chemicals) are exemplary heat and light stabilizers. Further, hindered phenols are commonly used as an antioxidant in the production of films. Some suitable hindered phenols include those available from Ciba Specialty Chemicals under the trade name IRGANOX™, such as IRGANOX™ 1076, 1010, or E 201. Moreover, bonding agents may also be added to the film to facilitate bonding of the film to additional materials (e.g., a nonwoven facing). Typically, such additives (e.g., tackifier, antioxidant, stabilizer, etc.) can each be present in an amount from about 0.001 wt. % to about 25 wt. %, in some embodiments, from about 0.005 wt. % to about 20 wt. %, and in some embodiments, from about 0.01 wt. % to about 15 wt. % of the film based on the total weight of the film.

Regardless of the particular film content, the film and/or the materials used to form the film may also be subjected to one or more additional processing steps. In one embodiment, for example, an elastomeric polymer employed in the film can be crosslinked, before, after, and/or during lamination to a nonwoven facing, to provide the film with enhanced elastic characteristics. Crosslinking may be induced by subjecting the polymer to electromagnetic radiation, such as ultraviolet light, electron beam radiation, natural and artificial radio isotopes (e.g., $\alpha$, $\beta$, and $\gamma$ rays), x-rays, neutron beams, positively-charged beams, laser beams, and so forth. The wavelength ("$\lambda$") of the electromagnetic radiation may be about 1000 nanometers or less, in some embodiments about 100 nanometers or less, and in some embodiments, about 1 nanometer or less. Electron beam radiation, for instance, typically has a wavelength of about 1 nanometer or less. The total dosage absorbed (in one or multiple steps) may likewise range from about 10 kilograys (kGy) to about 300 kGy, in some embodiments, from about 50 kGy to about 200 kGy, and in some embodiments, from about 75 to about 150 kGy. In addition, the energy level may range from about 10 kiloelectron volts (keV) to about 300 keV, such as from about 50 keV to about 200 keV, such as from about 75 keV to about 150 keV. Upon crosslinking, a three-dimensional crosslinked network may be formed that provides the material with additional elasticity in the machine direction, cross-machine direction, or both.

II. Nonwoven Facing

In addition to the elastic film, the elastic nonwoven laminate of the present disclosure may also include one or more nonwoven facing layers that can serve as an exterior surface of the laminate. The nonwoven facing layers, for instance, may comprise a nonwoven material, such as a spunbond web or a meltblown web. The spunbond or meltblown nonwoven facing can include a polyolefin, and, in some embodiments, can include a combination of a polyolefin and a polyolefin-based plastomer. For example, in some embodiments, the spunbond or meltblown nonwoven facing can include a polyethylene and a polyethylene-based plastomer or a polypropylene and a polypropylene-based plastomer. In other embodiments, the spunbond or meltblown nonwoven facing can include a combination of any of the following: polyethylene, polypropylene, a polyethylene-based plastomer, and/or a polypropylene-based plastomer.

Polyethylenes that can be used to form the nonwoven facing layer include conventional polyethylene and low density polyethylene (LDPE). Other suitable ethylene polymers are available from The Dow Chemical Company under the designations ASPUN™ (LLDPE), DOWLEX™ (LLDPE) and ATTANET™ (ULDPE). Other suitable ethylene polymers are described in U.S. Pat. No. 4,937,299 to Ewen, et al., U.S. Pat. No. 5,218,071 to Tsutsui et al., U.S. Pat. No. 5,272,236 to Lai, et al., and U.S. Pat. No. 5,278,272 to Lai, et al., which are incorporated herein in their entirety by reference thereto for all purposes.

In addition, polyethylene-based plastomers can be used in conjunction with the aforementioned polyethylenes when forming the spunbond or meltblown nonwoven facing layer. Such ethylene-based plastomers include ethylene-based copolymer plastomers available under the designation EXACT™ from ExxonMobil Chemical Company of Houston, Tex. Other suitable polyethylene plastomers are available under the designation ENGAGE™ and AFFINITY™ from Dow Chemical Company of Midland, Mich. An additional suitable polyethylene-based plastomer is an olefin block copolymer available from Dow Chemical Company of Midland, Mich. under the trade designation INFUSE™.

Of course, the present invention is by no means limited to the use of ethylene polymers. For instance, conventional polypropylene can be a component of the spunbond or meltblown nonwoven facing layer. Further, propylene plastomers may also be suitable for use in the nonwoven facing layers in combination with conventional polypropylene. Suitable plastomeric propylene polymers may include, for instance, copolymers or terpolymers of propylene, copolymers of propylene with an $\alpha$-olefin (e.g., $C_3$-$C_{20}$), such as ethylene, 1-butene, 2-butene, the various pentene isomers, 1-hexene, 1-octene, 1-nonene, 1-decene, 1-unidecene, 1-dodecene, 4-methyl-1-pentene, 4-methyl-1-hexene, 5-methyl-1-hexene, vinylcyclohexene, styrene, etc. The comonomer content of the propylene polymer may be about 35 wt. % or less, in some embodiments from about 1 wt. % to about 20 wt. %, and in some embodiments, from about 2 wt. % to about 10 wt. %. Preferably, the density of the polypropylene (e.g., propylene/$\alpha$-olefin copolymer) may be 0.91 $g/cm^3$ or less, in some embodiments, from 0.85 $g/cm^3$ to 0.88 $g/cm^3$, and in some embodiments, from 0.85 $g/cm^3$ to 0.87 $g/cm^3$. Suitable propylene polymers are commercially available under the designations VISTAMAXX™ (e.g., 6102), a propylene-based elastomer from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Other examples of suitable propylene polymers are described in U.S. Pat. No. 5,539,056 to Yang, et al., U.S. Pat. No. 5,596,052 to Resconi, et al., and U.S. Pat. No. 6,500,563 to Datta, et al., which are incorporated herein in their entirety by reference thereto for all purposes.

Regardless of the particular combination of polyolefins and/or polyolefin-based plastomers employed in the nonwoven facing layer(s) of the present disclosure, a polyolefin can be present in the nonwoven facing layer(s) in an amount up to about 100%, such as an amount ranging from about 40 wt. % to about 100 wt. %, such as an mount ranging from about 50 wt. % to about 99 wt. %, such as an amount ranging from about 60 wt. % to about 98 wt. % based on the total weight of the nonwoven facing layer(s). Meanwhile, a polyolefin-based plastomer can be present in the nonwoven facing layer(s) in an amount ranging from about 0.5 wt. % to about 60 wt. %, such as from about 1 wt. % to about 50 wt. %, such as from about 2 wt. % to about 40 wt. % based on total weight of the nonwoven facing layers.

Further, the fillers discussed above in Section I(c) in reference to the elastic film can also be utilized in the nonwoven web material of the present disclosure. When utilized, the amount of fillers present in the nonwoven facing can range from about 0.1 wt % to about 10 wt. %, in some embodiments, from about 0.5 wt. % to about 7.5 wt. %, and in some embodiments, from about 1 wt. % to about 5 wt. % of the nonwoven facing based on the total weight of the nonwoven facing.

Monocomponent and/or multicomponent fibers may be used to form the nonwoven web material. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art and so forth. Various methods for forming multicomponent fibers are described in U.S. Pat. No. 4,789,592 to Taniguchi, et al., U.S. Pat. No. 4,795,668 to Kruege, et al., U.S. Pat. No. 5,108,820 to Kaneko, et at, U.S. Pat. No. 5,336,552 to Strack, et al., U.S. Pat. No. 5,382,400 to Pike, et al., and U.S. Pat. No. 6,200,669 to Marmon, et al., which are incorporated herein in their entirety by reference thereto for all purposes. Multicomponent fibers having various irregular shapes may also be formed, such as described in U.S. Pat. No. 5,057,368 to Largman, et al., U.S. Pat. No. 5,069,970 to Largman, et al., U.S. Pat. No. 5,162,074 to Hills, U.S. Pat. No. 5,277,976 to Hogle, et al., and U.S. Pat. No. 5,466,410 to Hills, which are incorporated herein in their entirety by reference thereto for all purposes.

If desired, the nonwoven facing used to form the elastic nonwoven laminate of the present invention may have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al., U.S. Pat. No. 4,374,888 to Bornslaeger, U.S. Pat. No. 4,766,029 to Brock et al., U.S. Pat. No. 5,169,706 to Collier et al., U.S. Pat. No. 5,213,881 to Timmons et al., and U.S. Pat. No. 5,464,688 to Timmons, et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven facing may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven facing may be provided as two or more individually produced layers of a spunbond web, a meltblown web, etc., which have been bonded together to form the nonwoven facing. These individually produced layers may differ in terms of production method, basis weight, composition, etc. as discussed above.

The basis weight of each of the nonwoven facing layers may generally vary, such as from about 1 gsm to about 120 gsm, such as from about 5 gsm to about 80 gsm, such as from about 10 gsm to about 60 gsm, such as from about 15 gsm to about 40 gsm. When multiple nonwoven facings are utilized, such materials may have the same or different basis weights.

III. Lamination, Grooving and Bonding Techniques a. Lamination

Any of a variety of techniques may be employed to laminate the elastic film and nonwoven facing layers discussed above together to form the elastic nonwoven laminate of the present invention, including adhesive bonding, thermal bonding, ultrasonic bonding, microwave bonding, extrusion coating, and so forth. In one particular embodiment, nip rolls apply a pressure to the elastic film and nonwoven facing(s) to thermally bond the layers together. The rolls may be smooth and/or contain a plurality of raised bonding elements. In one embodiment, a laminate containing an elastic film sandwiched between two nonwoven facing layers can be formed. The rolls used to join the film to the nonwoven facing layers can be smooth chill rolls, and the nonwoven facing layers can be laminated to the film by extrusion casting the elastic film between two facing materials as the film and facing materials pass through the nip between the chilled rolls. In another embodiment, an already-cast film can be disposed between the nonwoven facing layers and adhesively bonded to the nonwoven facing layers. Adhesives that can be employed can include BOSTIK™ H2494 available from Bostik Findley, Inc, of Wauwatosa, Wis. and REXTAC™ 2730 and 2723 available from Huntsman Polymers of Houston, Tex. The type and basis weight of the adhesive used will be determined on the elastic attributes desired in the final composite and end use. For instance, the basis weight of the adhesive may be from about 0.5 gsm to about 3 gsm, such as from about 0.75 gsm to about 1.75 gsm, such as from about 1 gsm to about 1.5 gsm. The adhesive may be applied to the nonwoven web facings and/or the elastic material prior to lamination using any known technique, such as by ribbon, slot, melt spray, of dot pattern adhesive systems.

FIG. 1 schematically illustrates an exemplary process 100 for forming an elastic nonwoven laminate in this manner. Initially, an elastic film 126 is passed between a first set of nip rolls 132 and 134, and a second set of nip rolls 136 and 138. Further, nonwoven facing layers 124 and 128 are also unwound from storage rolls 122 and 130 and combined with the elastic film 126 to form a composite 140 between nip rolls 136 and 138. The layers may be combined with the aid of an adhesive applied to the nonwoven layers or the precursor layer, or with the aid of heat supplied from roll 136 and/or 138. After the composite 140 is formed, it may then be subjected to additional processing steps at location 146 (e.g., grooving, bonding, etc. as discussed below) before being wound onto a roll 144. Further, in some embodiments, prior to attaching the film to the nonwoven facings, the film can be e-beam crosslinked. In other embodiments, the film can be attached to a nonwoven facing on one side, then can be e-beam crosslinked, and then can be attached to a second nonwoven facing on the opposing side. For instance, when a facing contains polypropylene, it cannot be attached to the film prior to e-beam crosslinking because the polypropylene would degrade.

Although a three-layer laminate is shown in FIG. 1 having an elastic film, which itself can be multilayered (e.g., a core layer that provides elasticity sandwiched between two skin layers that provide strength or a core layer that provides strength sandwiched between two skin layers that provide elasticity) disposed between two nonwoven facings, other arrangements are also contemplated by the present disclosure. For instance, in one embodiment, a monolayered elastic film can be disposed between two nonwoven facing layers. In another embodiment, the elastic nonwoven laminate can include two film layers and three nonwoven facing layers. For example, the laminate can be arranged in the following order: spunbond facing, film, meltblown facing, film, spunbond facing, where the two film layers can be monolayered or multilayered. When the films are multilayered, the following arrangement is contemplated: spunbond facing, skin film layer, core film layer, meltblown facing, core film layer, skin film layer, spunbond facing. By having a meltblown facing disposed in the middle of the laminate, the resulting laminate can be provided with the desired level of loftiness.

Further, it is also to be understood that in addition to the method of forming the laminate discussed above, the film alternatively can be extrusion cast between nonwoven facing layers instead of being first cast and then adhesively bonded to the nonwoven facing layer(s).

b. Grooving

While only generally referenced at location 146 in FIG. 1, various additional potential processing and/or finishing steps known in the art, such as slitting, treating, printing graphics, etc., may be performed without departing from the spirit and scope of the invention. For instance, the laminate may be activated in the cross-machine and/or machine directions to enhance extensibility by decoupling the nonwoven facing from the elastic film of the laminate. In one embodiment, the composite may be coursed through two or more rolls that have grooves in the CD and/or MD directions. Such grooved satellite/anvil roll arrangements are described in U.S. Patent Application Publication Nos. 2004/0110442 to Rhim, et al. and 2006/0151914 to Gerndt, et al., which are incorporated herein in their entirety by reference thereto for all purposes. For instance, the laminate may be coursed through two or more rolls that have grooves in the CD and/or MD directions. The grooved rolls may be constructed of steel or other hard material (such as a hard rubber).

Figure 2:
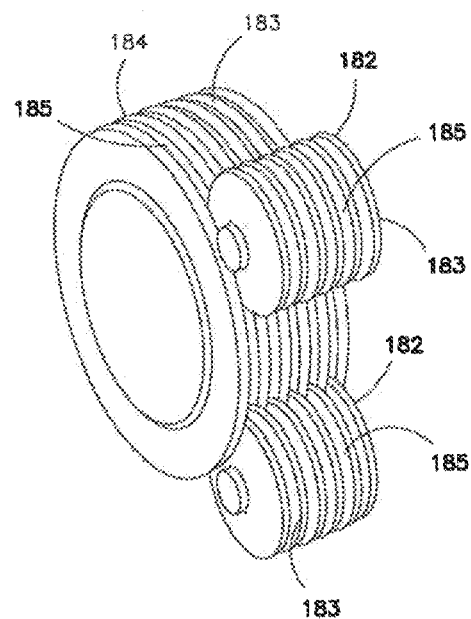
FIG. 2 is a perspective view of grooved rolls that may be used in one embodiment of the present invention.
Figure 3:
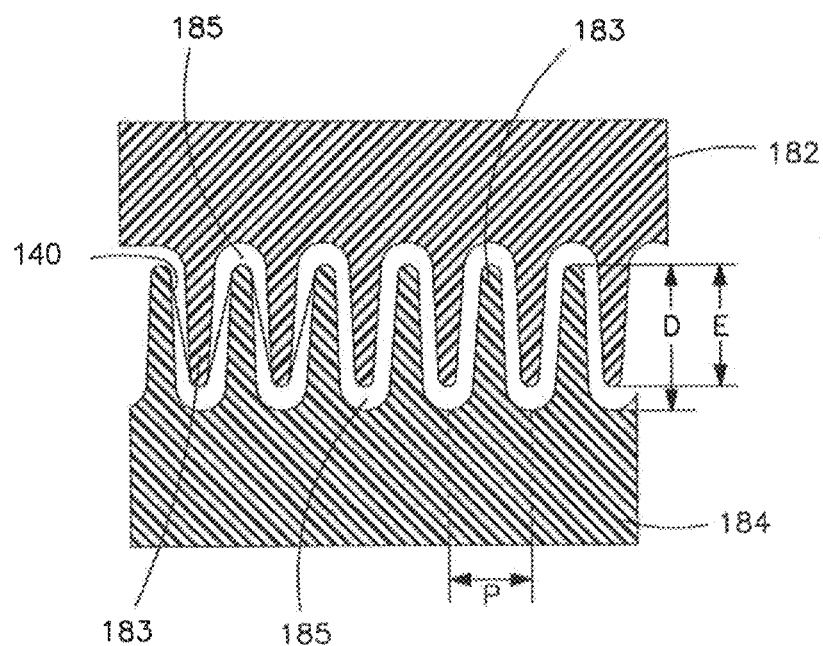
FIG. 3 is a cross-sectional view showing the engagement between two of the grooved rolls of FIG. 2.

FIGS. 2-3 further illustrate the manner in which groove rolls may decouple the nonwoven facing from the elastic portion of the composite. As shown, for example, satellite rolls 182 may engage an anvil roll 184, each of which include a plurality of ridges 183 defining a plurality of grooves 185 positioned across the grooved rolls in the cross-machine direction. The grooves 185 are generally oriented perpendicular to the direction of stretch of the material. In other words, the grooves 185 are oriented in the machine direction to stretch the composite in the cross-machine direction. The grooves 185 may likewise be oriented in the cross-machine direction to stretch the composite in the machine direction. The ridges 183 of satellite roll 182 intermesh with the grooves 185 of anvil roll 184, and the grooves 185 of satellite roll 182 intermesh with the ridges 183 of anvil roll 184.

The dimensions and parameters of the grooves 185 and ridges 183 may vary. In general, the groove rolls can include grooves that are evenly spaced along the length of the groove face or unevenly spaced. For example, the number of grooves 185 contained on a roll may generally range from about 1 and 12 grooves per inch, in some embodiments from about 2 and 10 grooves per inch, and in some embodiments, from about 3 and 8 grooves per inch. The grooves 185 may also have a certain depth "D", which generally ranges from about 0.05 inches to about 1 inch, in some embodiments, from about 0.075 inches to about 0.5 inches, and in some embodiments, from about 0.1 inches to about 0.3 inches. In addition, the peak-to-peak distance "P" between the grooves 185 is typically from about 0.05 inches to about 1 inch, in some embodiments from about 0.075 inches to about 0.5 inches, and in some embodiments, from about 0.1 inches to about 0.25 inches. Further, the laminate can be engaged at a depth ranging from about to about 90%, such as from about 30% to about 85%, such as from about 50% to 80% of the depth of the grooves.

If desired, heat may be applied to the composite or laminate just prior to or during the application of the grooves to cause it to relax somewhat and ease extension. Heat may be applied by any suitable method known in the art, such as heated air, infrared heaters, heated nipped rolls, or partial wrapping of the laminate around one or more heated rolls or steam canisters, etc. Heat may also be applied to the grooved rolls themselves. It should be also understood that other grooved roll arrangement are equally suitable, such as two grooved rolls positioned immediately adjacent to one another. In another embodiment, the process may include a grooved roll that contacts a flat anvil roll which may have a deformable surface.

Regardless of other formation techniques utilized, the laminate 140 (FIG. 3) may be stretched in one or more directions at a stretch ratio of from about 1.5 to about 8.0, in some embodiments by at least about 2.0 to about 6.0, and in some embodiments, from about 2.5 to about 4.5. The stretch ratio is determined by dividing the stretched length of a material by the original length of the material. In other words, the stretch ratio is equal to the original length of the material plus the change in length of the material upon stretching, divided by the original length, which is also the sum of the strain plus one.

c. Post-Bonding

After the laminate has been formed via attaching the elastic film to the nonwoven as discussed above, and after the nonwoven facing has been decoupled from the elastic film via grooving to activate machine direction and or cross-machine direction stretchability of the laminate, typically, with spunbond or meltblown nonwoven facings, the fibers in the nonwoven facing can separate from each other, pull out, and create a "fuzzy" appearance. These facings can also have insufficient shear and peel properties for use in certain absorbent article applications, which can prevent the use of meltblown or spunbond nonwoven facings in laminates where fiber pullout is a concern, such as in materials utilizing reusable fastening/attachment mechanisms.

Meanwhile, post-bonding of an outer surface of the nonwoven facing material can reduce fiber pull out and the fuzzy appearance of meltblown and spunbond nonwoven facings in laminates that have been groove-activated so that such laminates can be used in applications with minimal fiber pullout, yet without sacrificing the softness or feel of the laminates, nor their elastic stretchability and recoverability. Post-bonding of an outer-facing surface of nonwoven facing layer can generally be accomplished in the present invention via a smooth calendar roll or via a patterned bonding technique (e.g., thermal point bonding, ultrasonic bonding, etc.) in which the laminate is supplied to a nip defined by at least one patterned roll. Thermal point bonding, for instance, typically employs a nip formed between two rolls, at least one of which is patterned. Ultrasonic bonding, on the other hand, typically employs a nip formed between a sonic horn and a patterned roll. Regardless of the technique chosen, the patterned roll can contain a plurality of bonding elements to bond the film to the nonwoven web material(s) and, in some embodiments, form apertures in the nonwoven facing, such as when the laminate is used as a side panel in an absorbent article and should be breathable. The size of the bonding elements may be specifically tailored to enhance bonding of the nonwoven facing and can also be selected to facilitate the formation of apertures in the nonwoven facing and, in some embodiments, the film layer of the laminate. For example, the bonding elements are typically selected to have a relatively large length dimension. The length dimension of the bonding elements may be from about 300 to about 5000 micrometers, in some embodiments from about 500 to about 4000 micrometers, and in some embodiments, from about 1000 to about 2000 micrometers. The width dimension of the bonding elements may likewise range from about 20 to about 500 micrometers, in some embodiments from about 40 to about 200 micrometers, and in some embodiments, from about 50 to about 150 micrometers. In addition, the "element aspect ratio" (the ratio of the length of an element to its width) may range from about 2 to about 100, in some embodiments from about 4 to about 50, and in some embodiments, from about 5 to about 20.

Besides the size of the bonding elements, the overall bonding pattern may also be selectively controlled to achieve the desired bond formation on an outer surface of the nonwoven facing. In one embodiment, the nonwoven facing layer(s) can be point unbonded or "PUB" bonded. "Point unbonded" or "PUB" bonding means a facing pattern having continuous bonded areas defining a plurality of discrete unbonded areas. The fibers or filaments within the discrete unbonded areas are dimensionally stabilized by the continuous bonded areas that encircle or surround each unbonded area and the unbonded areas are specifically designed to afford spaces between fibers or filaments within the unbonded areas. A suitable process for forming the pattern-unbonded nonwoven facing of the present invention includes providing a nonwoven facing, providing oppositely positioned first and second calender rolls and defining a nip therebetween, with at least one of said rolls being heated and having a bonding pattern on its outermost surface comprising a continuous pattern of land areas defining a plurality of discrete openings, apertures or holes, and passing the nonwoven facing within the nip formed by said rolls. Each of the openings in said roll or rolls defined by the continuous land areas forms a discrete unbonded area in at least one surface of the nonwoven facing in which the fibers or filaments of the facing are substantially or completely unbonded. Stated alternatively, the continuous pattern of land areas in said roll or rolls forms a continuous pattern of bonded areas that define a plurality of discrete unbonded areas on at least one surface of said nonwoven facing.

Figure 4:
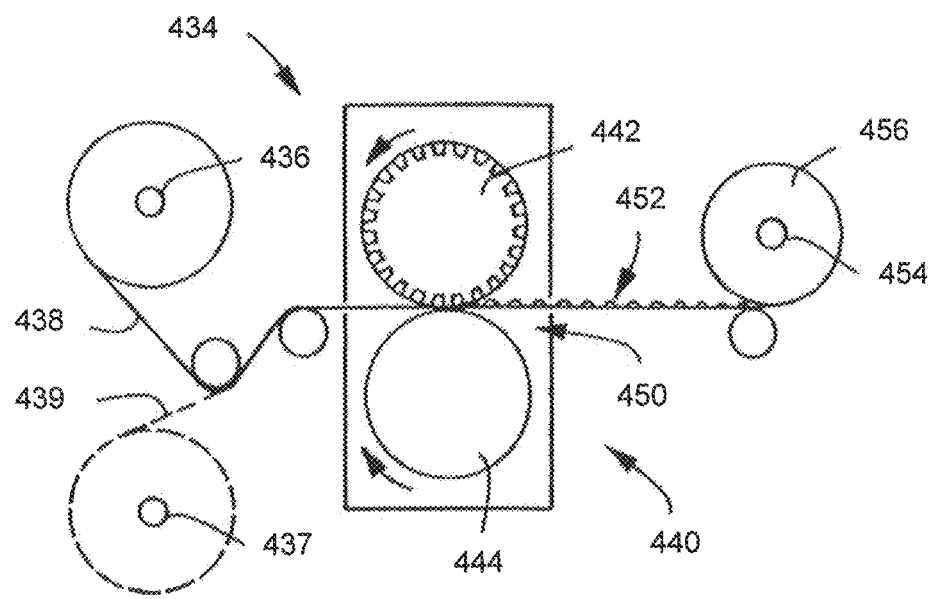
FIG. 4 is a schematic side view of an apparatus for making a pattern unbonded (PUB) nonwoven material in accordance with one embodiment of the present invention.
Figure 5:
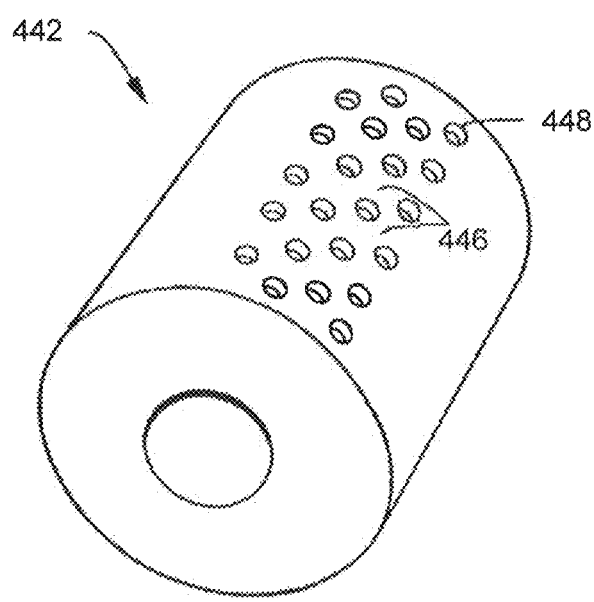
FIG. 5 is a perspective view of a patterned roll that can be used in accordance with the apparatus of FIG. 4.

After the laminate of the present invention is formed, the laminate is passed through a suitable process and apparatus to form the pattern-unbonded nonwoven loop material of the present invention. Referring now to FIGS. 4 and 5, a process and apparatus for forming the pattern-unbonded nonwoven facing of the present invention now will be described. In FIG. 4, apparatus for forming the pattern-unbonded nonwoven loop material of this invention is represented generally as element 434. The apparatus includes a first facing unwind 436 for a first laminate 438. Optionally, one or more additional rolls 437 (shown in phantom) for additional laminates 439 may be employed in forming multi-layer pattern-unbonded laminates. It should be understood that although the apparatus shown in FIG. 4 illustrates a laminate unwind 436, the pattern-unbonding assembly 400 may be placed in a continuous (in-line) process with the laminate forming equipment described herein, as shown in FIG. 1 as reference numeral 146. As used herein, the term "pattern-unbonding assembly" should not be construed as apparatus for disassembling, destroying or removing existing bonds, if any, in laminate 438; rather, pattern-unbending assembly refers to an apparatus that continuously bonds or fuses the fibers or filaments forming the nonwoven facing of laminate 438 in specified areas of the web, and prevents bonding or fusing of the fibers or filaments of the nonwoven facing of laminate 438 in other specified areas of the web, such areas being referred to herein as bonded areas and unbonded areas, respectively.

First laminate 438 is taken off the unwind 436 and passed into a pattern-unbonding assembly 400 that includes a first or patterned roll 442 and a second or anvil roll 444, both of which are driven by conventional drive means, such as, for example, electric motors (not shown). Patterned roll 442 is a right circular cylinder that may be formed of any suitable, durable material, such as, for example, steel, to reduce wear on the rolls during use. Patterned roll 442 has on its outermost surface a pattern of land areas 446 that define a plurality of discrete openings or apertures 448. The land areas 446 are designed to form a nip with the smooth or flat outer surface of oppositely positioned anvil roll 444, which also is a right circular cylinder that can be formed of any suitable, durable material.

Figure 6:
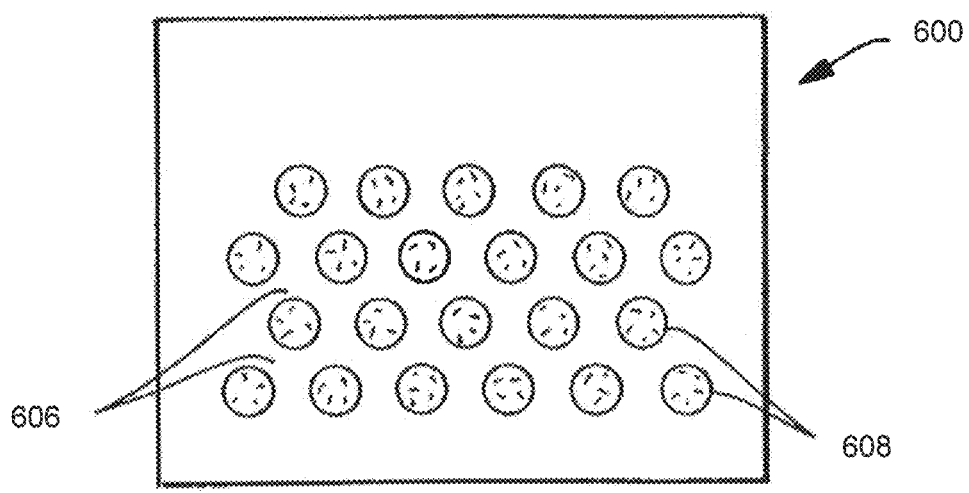
FIG. 6 is a top view of a pattern unbonded nonwoven material formed in accordance with one embodiment of the present invention.

The size, shape, number, and configuration of openings 448 in patterned roll 442 can be varied to meet the particular end-use needs of the pattern-unbonded nonwoven facing of the laminate being formed thereby. In order to reduce the incidence of fiber pull-out in the resulting laminate material, the size of openings 448 in patterned roll 442 can be dimensioned to reduce the likelihood that the entire length of the filaments or fibers forming an unbonded area will lie within a single unbonded area, Stated differently, fiber length should be selected to reduce the likelihood that the entire length of a given fiber or filament will fall within a single unbonded area. On the other hand, the desirability of restricting the size of the openings 448 in patterned roll 442, and the unbonded areas 608 formed thereby in the pattern-unbonded nonwoven facing 600 of FIG. 6, is counterbalanced by the need for the unbonded areas 608 to have sufficient size to provide the required engagement areas for the hook elements of a complementary hook material, in applications where, for example, the elastic nonwoven laminates is used as part of a fastening system in an absorbent article. The bonding areas can also be minimized so that the resulting laminate material maintains a desired level of loftiness.

Circular openings 448 as shown in FIG. 5 hereof having an average diameter ranging from about 0.050 inch (about 0.127 cm) to about 0.250 inch (about 0.635 cm), such as from about 0.130 inch (0.330 cm) to about 0.160 inch (0.406 cm), and a depth measured from the outermost surface of patterned roll 442 of at least about 0.020 inch (about 0.051 cm), such as from about 0.060 inch (0.152 cm), are considered suitable in forming the pattern-unbonded nonwoven material of the present invention. While openings 448 in patterned roll 442 as shown in FIG. 5 are circular, other shapes, such as ovals, squares, diamonds and the like can be advantageously employed.

The number or density of openings 448 in patterned roll 442 also can be selected to provide the requisite amount of engagement areas for, for instance, hook elements in an absorbent article, without unduly limiting the size of the continuous bonded areas and giving rise to increased incidence of fiber pull-out. Pattern rolls having an opening density in the range of from about 1 opening per square centimeter ($cm^2$) to about 25 openings/$cm^2$, such as from about 5 openings/$cm^2$ to about 7 openings/$cm^2$, may be utilized to advantage in forming the pattern-unbonded nonwoven facing in the laminate of the present invention.

Moreover, the spacing between individual openings 448 can be selected to enhance the hook engagement functionality of the resulting laminate including the pattern-unbonded nonwoven facing, which can, in some embodiments, be used as a loop material, without overly reducing the portion of the pattern-unbonded loop material occupied by continuous bonded areas, which serve to lessen fiber pull-out. Suitable inter-opening spacings for the embodiment shown can range from about 0.13 inch (about 3.30 mm) to about 0.22 inch (about 5.59 mm), centerline-to-centerline, in the machine and cross-machine directions, The particular arrangement or configuration of openings 448 in patterned roll 442 is not considered critical, so long as in combination with the opening size, shape and density, the desired levels of surface integrity, loftiness, durability, peel strength, etc. can be achieved. For example, as shown in FIG. 5, the individual openings 448 are arranged in staggered rows. Other different configurations are considered within the scope of the present invention.

The portion of the outermost surface of the patterned roll 442 occupied by continuous land areas 446 likewise can be modified to satisfy the contemplated end-use application of the pattern-unbonded material. The degree of bonding imparted to the pattern-unbonded nonwoven facing of the laminate by the continuous land areas 446 can be expressed as a percent bond area, which refers to the portion of the total plan area of at least one outer surface of a pattern-unbonded nonwoven facing 600 (see FIG. 6) that is occupied by bonded areas 606 and unbonded areas 608. Stated generally, the lower limit on the percent bond area suitable for forming the pattern-unbonded nonwoven facing 600 of the present invention is the point at which fiber pull-out excessively reduces the surface integrity and durability of the pattern-unbonded material. The required percent bond area will be affected by a number of factors, including the type(s) of polymeric materials used in forming the fibers or filaments of the nonwoven facing, whether the nonwoven facing is a single- or multi-layer fibrous structure, whether the nonwoven facing is unbonded or pre-bonded prior to passing into the pattern-unbonding assembly, and the like. Pattern-unbonded nonwoven facings having percent bond areas ranging from about 10% to about 60%, such as from about 15% to about 55%, such as from about 20% to about 50% based on the total surface area of the nonwoven facing, have been found suitable.

The temperature of the outer surface of patterned roll 442 can be varied by heating or cooling relative to anvil roll 444. Heating and/or cooling can affect the features of the laminate(s) being processed and the degree of bonding of single or multiple laminates being passed through the nip formed between the counterrotating patterned roll 442 and anvil roll 444. In the embodiment shown in FIG. 4, for example, both patterned roll 442 and anvil roll 444 are heated, desirably to the same bonding temperature. The specific ranges of temperatures to be employed in forming the pattern-unbonded nonwoven facing is dependent upon a number of factors, including the types of polymeric materials employed in forming the pattern-unbonded nonwoven facing, the inlet or line speed(s) of the nonwoven web(s) passing through the nip formed between patterned roll 442 and anvil roll 444, and the nip pressure between patterned roll 442 and anvil roll 444.

Anvil roll 444 as shown in FIG. 4 has an outer surface that is much smoother than patterned roll 442, and preferably is smooth or flat. It is possible, however, for anvil roll 444 to have a slight pattern on its outer surface and still be considered smooth or flat for purposes of the present invention. For example, if anvil roll 444 is made from or has a softer surface, such as resin impregnated cotton or rubber, it will develop surface irregularities, yet it will still be considered smooth or flat for purposes of the present invention. Such surfaces are collectively referred to herein as "flat," Anvil roll 444 provides the base for patterned roll 442 and the web or webs of material to contact. Typically, anvil roll 444 will be made from steel, or materials such as hardened rubber, resin-treated cotton or polyurethane.

Alternatively, anvil roll 444 may be replaced with a pattern roll (not shown) having a pattern of continuous land areas defining a plurality of discrete, apertures or openings therein, as in the above-described patterned roll 442. In such case, the pattern-unbonding assembly would include a pair of counter-rotating pattern rolls which would impart a pattern of continuous bonded areas defining a plurality of discrete unbonded areas on both the upper and lower surfaces of the pattern-unbonded nonwoven loop material. Rotation of the oppositely positioned pattern rolls can be synchronized, such that the resulting unbonded areas on the surfaces of the pattern-unbonded material are vertically aligned or juxtaposed.

Referring again to FIG. 4, patterned roll 442 and anvil roll 444 are rotated in opposite directions to one another so as to draw the nonwoven facing(s) through the nip area defined therebetween. Patterned roll 442 has a first rotational speed measured at its outer surface and anvil roll 444 has a second rotational speed measured at its outer surface. In the embodiment shown, the first and second rotational speeds are substantially identical. However, the rotational speeds of the pattern and anvil rolls can be modified to create a speed differential between the counter-rotating rolls.

The locations of the oppositely positioned patterned roll 442 and anvil roll 444 may be varied to create a nip area 450 between the rolls. The nip pressure within nip area 450 can be varied depending upon the properties of the web itself or webs themselves and the degree of bonding desired. Other factors that will allow variances in the nip pressure will include the temperatures of the patterned roll 442 and anvil roll 444, the size and spacing of openings 448 in patterned roll 442, as well as the types of polymeric materials used in forming the pattern-unbonded nonwoven material. With respect to the degree of bonding to be imparted to the pattern-unbonded nonwoven loop material within the continuous bonded areas, the pattern-unbonded material desirably is thoroughly bonded or melt-fused in the bonded areas, such that the polymeric material is rendered non-fibrous. This high degree of bonding is important in stabilizing the portions of the fibers or filaments within the unbonded areas extending into the continuous bonded areas and reducing fiber pull-out when, for example, hook elements for a fastening mechanism are disengaged from the discrete unbonded areas.

In another embodiment, for example, a bonding pattern is selected in which the longitudinal axis (longest dimension along a center line of the element) of one or more of the bonding elements is skewed relative to the machine direction ("MD") of the laminate. For example, one or more of the bonding elements may be oriented from about 30° to about 150°, in some embodiments from about 45° to about 135°, and in some embodiments, from about 60° to about 120° relative to the machine direction of the laminate. In this manner, the bonding elements will present a relatively large surface to the laminate in a direction substantially perpendicular to that which the laminate moves.

The pattern of the bonding elements is generally selected so that the nonwoven facing has a total bond area of less than about 50% (as determined by conventional optical microscopic methods), and in some embodiments, less than about 30%. The bond density is also typically greater than about 50 bonds per square inch, and in some embodiments, from about 75 to about 500 pin bonds per square inch. One suitable bonding pattern for use in the present invention is known as an "S-weave" pattern and is described in U.S. Pat. No. 5,964,742 to McCormack et al., which is incorporated herein in its entirety by reference thereto for all purposes.

Figure 7:
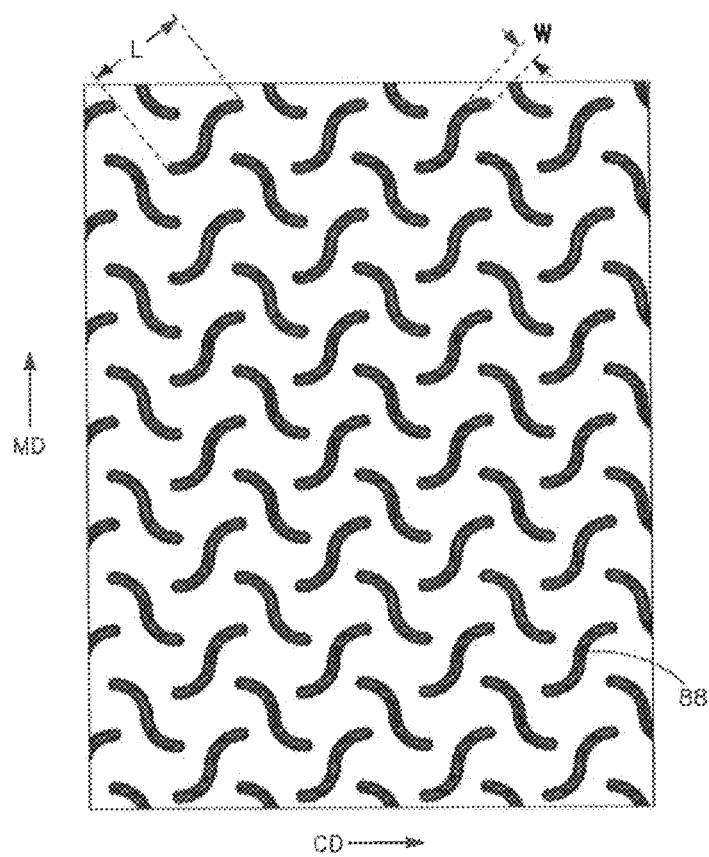
FIG. 7 illustrates one embodiment of an "S-weave" bonding pattern that may be used in accordance with the present invention.
Figure 8:
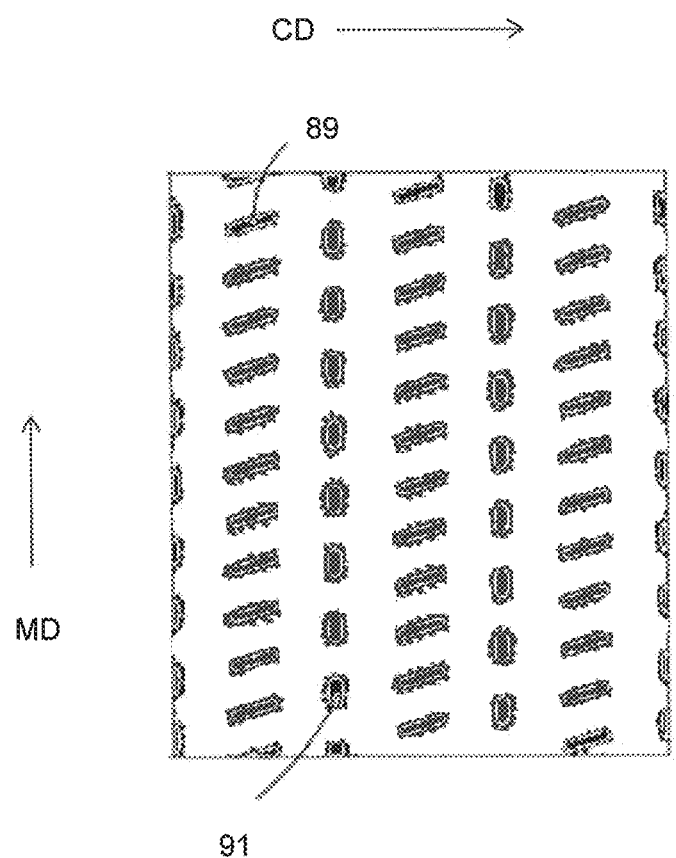
FIG. 8 illustrates one embodiment of a "rib-knit" bonding pattern that may be used in accordance with the present invention.
Figure 9:
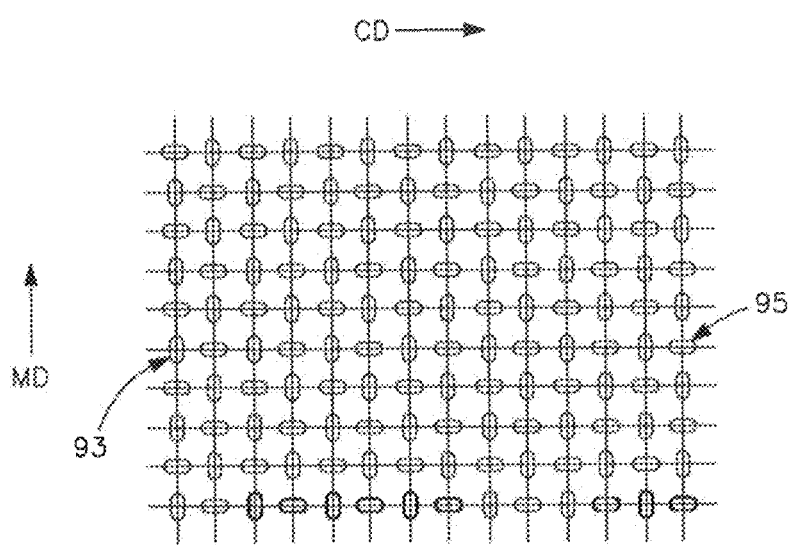
FIG. 9 illustrates one embodiment of a "wire-weave" bonding pattern that may be used in accordance with the present invention.

S-weave patterns typically have a bonding element density of from about 50 to about 500 bonding elements per square inch, and in some embodiments, from about 75 to about 150 bonding elements per square inch. An example of a suitable "S-weave" pattern in shown in FIG. 7, which illustrates S-shaped bonding elements 88 having a length dimension "L" and a width dimension "W." Another suitable bonding pattern is known as the "rib-knit" pattern and is described in U.S. Pat. No. 5,620,779 to Levy, et al., which is incorporated herein in its entirety by reference thereto for all purposes. Rib-knit patterns typically have a bonding element density of from about 150 to about 400 bonding elements per square inch, and in some embodiments, from about 200 to about 300 bonding elements per square inch. An example of a suitable "rib-knit" pattern in shown in FIG. 8, which illustrates bonding elements 89 and bonding elements 91, which are oriented in a different direction, Yet another suitable pattern is the "wire weave" pattern, which has a bonding element density of from about 200 to about 500 bonding elements per square inch, and in some embodiments, from about 250 to about 350 bonding elements per square inch. An example of a suitable "wire-weave" pattern in shown in FIG. 9, which illustrates bonding elements 93 and bonding elements 95, which are oriented in a different direction. Still another suitable pattern is a "modified high density diamond" (MHDD) pattern. Other bond patterns that may be used in the present invention are described in U.S. Pat. No. 3,855,046 to Hansen et al., U.S. Pat. No. 5,962,112 to Haynes et al., U.S. Pat. No. 6,093,665 to Sayovitz et al., U.S. Pat. No. 0,375,844 to Edwards, et al., D390,708 to Brown, and D428,267 to Romano et al., which are incorporated herein in their entirety by reference thereto for all purposes. Although the patterned rolls discussed above are generally utilized to bond the nonwoven facings of the present invention, such rolls, as briefly mentioned above, can also be used to form apertures in the nonwoven facings. In some embodiments, vacuum aperturing processes can also be used.

The selection of an appropriate bonding temperature (e.g., the temperature of a heated roll) will help melt and/soften the polymer(s) of the nonwoven facing at regions adjacent to the bonding elements. The softened polymer(s) may then flow and become displaced during bonding, such as by pressure exerted by the bonding elements. The displaced portions of the nonwoven facing can also fuse to other portions of the nonwoven facing, thereby reducing the fuzziness and reducing the fiber-pullout from the nonwoven facing typically experienced when bonded carded webs and other meltblown and spunbond nonwoven webs are utilized in a nonwoven facing. To achieve such bond formation on the nonwoven facing, the bonding temperature, pressure, and nip speed may be selectively controlled. For example, one or more rolls may be adjusted to a surface temperature of from about 65° F. to about 300° F., in some embodiments from about 175° F. to about 250° F., and in some embodiments, from about 180° F. to about 240° F. Likewise, the pressure exerted by the bond rolls ("nip pressure") during thermal bonding of the nonwoven facing may range from about 5 pound per square inch (psi) to about 100 psi, such as from about 10 psi to about 65 psi, such as from about 15 psi to about 60 psi, such as from about 20 psi to about 50 psi. Further, in some embodiments, the post-bond temperature can range from about 190° F. to about 210° F. and, the post-bond pressure can range from about 10 psi to about 35 psi. In still other embodiments, the post-bonding can be carried out at ambient temperature, such as from about 65° F. to about 75° F., to about 150° F., because of the sensitivity of the laminate to heat, such as when an olefin-based elastomer such as VISTAMAXX™ is utilized, as such polymers may lose some of their elasticity when heated. Even using such low post-bond temperatures and pressures, the present inventors have discovered that a spunbond or meltblown laminate can be formed. Of course, it should be understood that the residence time of the materials may influence the particular bonding parameters employed. In addition, in some embodiments, the nip speed during bonding can range from about 1 foot per minute (fpm) to about 60 fpm, such as from about 10 fpm to about 50 fpm, such as from about 15 fpm to about 40 fpm. Meanwhile, in other embodiments, the nip speed can range from about 100 fpm to about 3000 fpm, such as from about 250 fpm to about 2500 fpm, such as from about 500 fpm to about 2000 fpm.

Generally, as a result of the techniques discussed herein, spunbond or meltblown nonwoven facings containing a polypropylene homopolymer with a polypropylene-based elastomer or a polyethylene homopolymer with a polyethylene-based elastomer. The elastomers can provide the nonwoven facing with the desired level of softness, while at the same time allowing for easier grooving of the nonwoven facing compared to if only polypropylene or polyethylene are utilized, which is a possibility although such facings would be more loosely configured or fuzzy. Because the grooving of such nonwoven facings is easier to accomplish, there is less risk of damaging an underlying elastic film in laminates containing the aforementioned nonwoven facings.

In reference to spunbond nonwoven facings particularly, incorporating an ethylene-based elastomer such as INFUSE™ or a polypropylene-based elastomer such as VERSIFY™ with a polyethylene or a polypropylene creates a softer nonwoven facing that can be more easily grooved than a nonwoven facing containing polyethylene as the only olefinic polymer. Likewise, incorporating a polypropylene-based elastomer such as VISTAMAXX™ with a polypropylene can create a softer nonwoven facing that can be more easily grooved compared to a nonwoven facing containing polypropylene as the only olefinic polymer.

Further, in reference to meltblown nonwoven facings in particular, because meltblown facings generally include polymers having a lower molecular weight than other facings and also are less tacky and not bonded when initially formed, which means that meltblown facings can be grooved more easily. Moreover, polypropylene meltblown facings can be grooved more easily than polyethylene meltblown facings because polypropylene is more brittle than polyethylene, which is softer. In addition, post-bonding of polyethylene-based meltblown facings can be carried out at lower temperatures and pressures because of their lower molecular weights compared to spunbond facings and facings based on polymers other than polyethylene.

However, regardless of whether the facings of the present invention are polyethylene-based, polypropylene-based, spunbond, or meltblown, the film components, facing components, grooving conditions, and bonding conditions can be selected to achieve an elastic nonwoven laminate that has the desired levels of softness and elasticity with reduced fuzziness, while at the same exhibiting enhanced hook engagement and resisting fiber pullout, such as when the elastic nonwoven laminates are used in absorbent article applications utilizing hook or tab fastening means. For instance, when a tab or hook is attached to a laminate of the present invention that has been post bonded with smooth rolls, the elongation at failure (% elongation) of the tab or hook, which corresponds with hook disengagement, can range from about 50% to about 200%, such as from about 75% to about 190%, such as from about 100% to about 180%. Likewise, when a tab or hook is attached to a laminate of the present invention that has been post-bonded using a wire-weave pattern, the elongation at failure (% elongation) of the tab or hook can range from about 50% to about 150%, such as from about 60% to about 125%, such as from about 70% to about 100%.

Further, when a tab or hook is attached to a laminate of the present invention that has been post bonded with smooth rolls, the load at failure can range from about 600 grams-force to about 2200 grams-force, such as from about 800 grams-force to about 2100 grams-force, such as from about 1000 grams-force to about 2000 grams-force. Meanwhile, when a tab or hook is attached to a laminate of the present invention that has been post-bonded using a wire-weave pattern, the load at failure can range from about 400 grams-force to about 1200 grams-force, such as from about 500 grams-force to about 1100 grams-force, such as from about 600 grams-force to about 1000 grams-force.

The components of the elastic nonwoven laminates of the present invention can also be selectively controlled to achieve the desired tensile properties. For instance, elastic nonwoven laminates post-bonded with smooth rolls can exhibit a percent elongation of greater than about 200%, such as greater than about 400%, such as greater than about 800%. Further, elastic nonwoven laminates post-bonded using a wire-weave pattern can exhibit a percent elongation of greater than about 200%, such as from about 200% to about 1000%, such as from about 400% to about 800%. In addition, elastic nonwoven laminates post-bonded using a wire-weave pattern can exhibit a load at failure of greater than about 3000 grams-force, such as greater than about 4000 grams-force, such as greater than about 5000 grams-force. Meanwhile, elastic nonwoven laminates post-bonded using a wire-weave pattern can exhibit a load at failure of from about 1000 grams-force to about 4250 grams-force, such as from about 1500 grams-force to about 4000 grams-force, such as from about 2000 grams-force to about 3750 grams-force.

Further, the laminates of the present invention can exhibit a load loss of less than about 60%, such as from about 10% to about 60%, such as from about 15% to about 55%, such as from about 30% to about 50%, which is indicative that even with post-bonding, the laminates of the present invention maintain their elastic properties.

IV. Frangible Layer

Although the elastic nonwoven laminates discussed above have been described as including an elastic film attached to one or more nonwoven facings, it is also to be understood that the elastic nonwoven laminates of the present invention can also include one or more frangible layers located outside the one or more facings layers or disposed between the one or more facing layers and the elastic film. Such frangible layers are described in U.S. patent application Ser. No. 13/720,194, filed on Dec. 19, 2012, which is incorporated herein in its entirety by reference thereto for all purposes. Generally, the frangible layer can also be grooved in the manner described in reference to the nonwoven facings. The frangible layer can be used to add loftiness to the elastic nonwoven laminates of the present invention or to achieve the desired aesthetics depending on the particular application.

V. Articles

The elastic nonwoven laminate of the present invention may be used in a wide variety of applications. As noted above, for example, the elastic nonwoven laminate may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Absorbent articles may include a substantially liquid-impermeable layer (e.g., outer cover), a liquid-permeable layer (e.g., bodyside liner, surge layer, etc.), and an absorbent core. In one particular embodiment, the elastic nonwoven laminate of the present invention may have a wide variety of other uses, such as in providing an elastic waist, leg cuff/gasketing, stretchable ear, side panel, outer cover, or any other component in which elastic properties are desirable.

Figure 10:
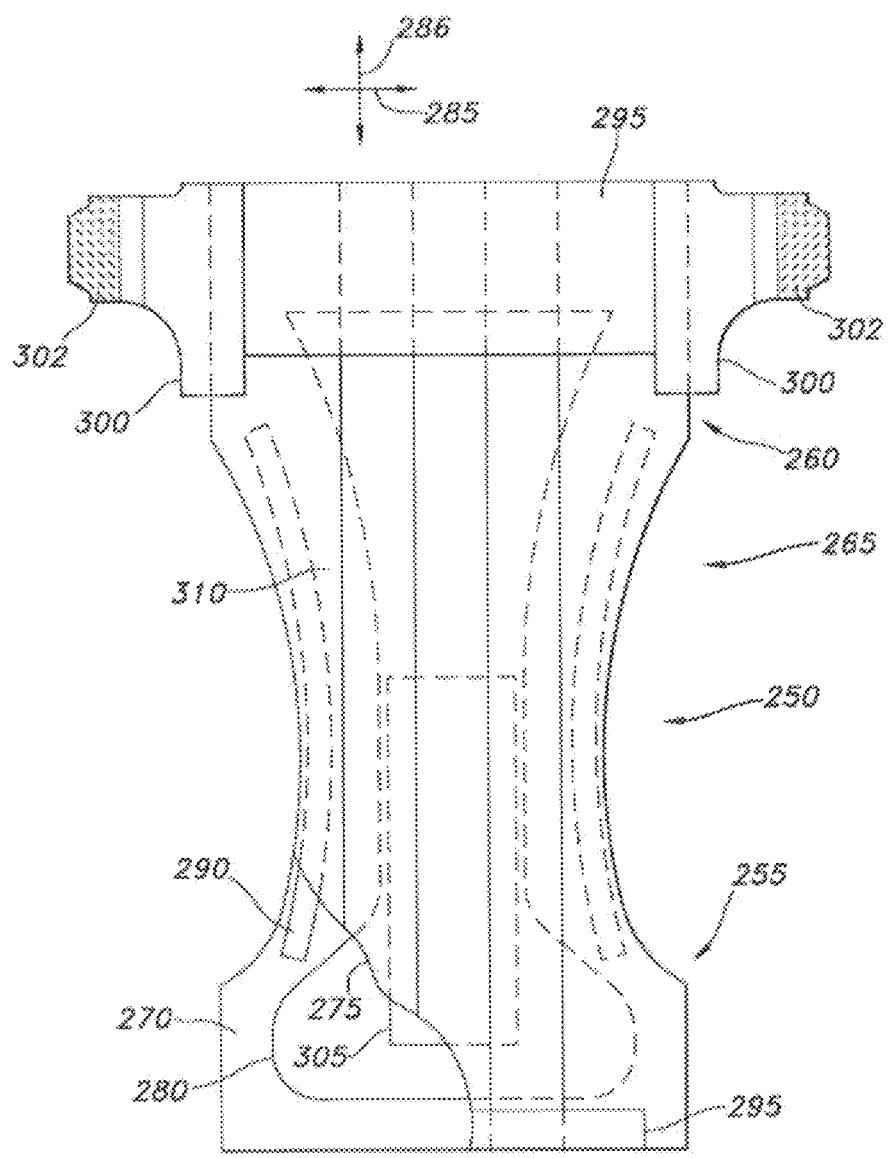
FIG. 10 is a top view of an absorbent article that may be formed in accordance with one embodiment of the present invention.

Referring to FIG. 10, for example, one embodiment of a disposable diaper 250 is shown that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members such as the elastic nonwoven composite of the present invention, as further explained below. For example, as representatively illustrated in FIG. 10, the diaper 250 may include leg/cuff gasketing 290 constructed to operably tension the side margins of the diaper 250 and closely fit around the legs of the wearer to reduce leakage and provide improved comfort and appearance. Waistbands 295 are employed that provide a resilient, comfortably close fit around the waist of the wearer. The elastic nonwoven laminate of the present invention is suitable for use as the leg/cuff gasketing 290 and/or waistbands 295. Examples of such materials are laminates sheets that either comprise or are adhered to the backsheet, such that elastic constrictive forces are imparted to the backsheet 270.

As is known, fastening means, such as hook and loop fasteners, may be employed to secure the diaper 250 on a wearer. Alternatively, other fastening means, such as buttons, pins, snaps, adhesive tape fasteners, cohesives, fabric-and-loop fasteners, or the like, may be employed. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may contain the elastic material of the present invention. Examples of absorbent articles that include side panels and selectively configured fastener tabs are described in PCT Patent Application WO 95/16425 to Roessler and U.S. Pat. No. 5,399,219 to Roessler et al., U.S. Pat. No. 5,540,796 to Fries, and U.S. Pat. No. 5,595,618 to Fries, each of which is incorporated herein in its entirety by reference thereto for all purposes.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 10, the disposable diaper 250 may also include a pair of containment flaps 310 which are configured to provide a barrier to the lateral flow of body exudates and which can be formed from the elastic nonwoven laminates of the present invention. The containment flaps 310 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearer's body. The containment flaps 310 may extend longitudinally along the entire length of the liquid retention structure 280 or may only extend partially along the length of the liquid retention structure. When the containment flaps 310 are shorter in length than the liquid retention structure 280, the containment flaps 310 can be selectively positioned anywhere along the side edges of the diaper 250 in the intermediate section 265. Such containment flaps 310 are generally well known to those skilled in the art. For example, suitable constructions and arrangements for containment flaps 310 are described in U.S. Pat. No. 4,704,116 to Enloe.

The various regions and/or components of the diaper 250 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the leg/cuff gasketing 290, waistband 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth. Several examples of such absorbent articles are described in U.S. Pat. No. 5,649,916 to DiPalma, et al., U.S. Pat. No. 6,110,158 to Kielpikowski, and U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell, et al., as well as U.S. Pat. No. 4,886,512 to Damico et al., U.S. Pat. No. 5,558,659 to Sherrod, et al., U.S. Pat. No. 6,511,465 to Freiburger, et al., and U.S. Pat. No. 6,888,044 to Fell, et al., all of which are incorporated herein in their entirety by reference thereto for all purposes. Of course, the elastic material is versatile and may also be incorporated into a wide variety of other types of articles. For example, the elastic material may be incorporated into a medical garment, such as gowns, caps, drapes, gloves, facemasks, etc.; industrial workwear garment, such as laboratory coats, coveralls, etc.; and so forth.

The present invention may be better understood with reference to the following examples.

Test Methods

Tensile Testing:

Tensile measurements were conducted on various samples using an MTS Sintech 1/S electro-mechanical tensile test frame equipped with MTS Test Works data acquisition software. The cross-head speed used was 20 inches/minute. Rectangular specimens having dimensions of 3 inches by 7 inches were loaded in the jaws of the frame at a grip to grip distance of 3 inches. The load-displacement data was collected at specified time intervals. From knowledge of the load and displacement, the elongation at break (%) and corresponding load at failure (gram-force) were obtained. The tests were conducted under ambient conditions.

Stress Relaxation Testing:

Stress relaxation testing was also carried out on an MTS Sintech 1/S electro-mechanical tensile test frame. The test specimen was clamped between the jaws at a 3 inch grip to grip distance. The sample and the grip fixtures were enclosed in an environmental chamber. The sample, after clamping, was equilibrated at 100° F. (about 37° C.) for 3 minutes. The sample was then elongated to a final constant elongation of 4.5 inches (50% elongation) at a cross-head displacement speed of 20 inches/minute. The load required to maintain the 50% elongation as a function of time was monitored. The data was acquired using MTS Sintech Test Works data acquisition software.

From a plot of the log load versus log time, the slope was determined and compared with an ideal elastic, which would have a slope of zero. The percentage loss of load at the end of the experiment was then determined. The load loss was obtained from a knowledge of the initial load and final load using the following equation: (Initial Load-Final Load)/(Initial Load)×100.

Hook Engagement Testing:

Hook engagement testing was also carried out on an MTS Sintech 1/S electro-mechanical tensile test frame. A modified ASTM D3163 lap shear test method was used to assess the shear force required for the pull-out of hooks off of various CD stretched laminates. A 1 inch wide by 5 inch long hook (tab) sample was attached at a 1 inch depth perpendicular to the stretch direction and in the middle of an elastic laminate that was 3 inches wide by 5 inches long. The tab was placed in the upper grip while the other end of the elastic laminate was placed in the bottom grip of the test frame. Each laminate sample was placed in the grips such that the center of the hook was 1.5 inches from the upper jaw. From knowledge of the load displacement data obtained using Test Works data acquisition software at a data sampling rate of 10 Hertz, the percent elongation and load at failure were obtained.

Example 1

A film containing 90 wt. % of a core layer and two 5 wt. % skin layers was extruded. The film components are shown below in Table 1.

TABLE 1

|  | Wt. % |
| --- | --- |
| 90 wt. % core layer | |
| SBS (KRATON ™ D1102) | 39.5 |
| SIBS (KRATON ™ D1171) | 58 |
| IRGANOX ™ 1010 Antioxidant | 0.5 |
| IRGAFOS ™ 168 Stabilizer | 0.5 |
| TiO$_2$ Filler (SCC 11692) | 1.5 |
| Total | 100 |
| 10 wt. % Skin Layers | |
| (2 Layers at 5 wt. % Each) | |
| LLDPE (DOWLEX ™ 2517) | 59 |
| LLDPE (DOWLEX ™ 2047) | 39.5 |
| TiO$_2$ Filler (SCC 11692) | 1.5 |
| Total | 100 |

Example 2

A film containing 90 wt % of a core layer and two 5 wt. % skin layers was extruded. The film components are shown below in Table 2.

TABLE 2

|  | Wt. % |
| --- | --- |
| 90 wt. % Core Layer | |
| VISTAMAXX ™ 6102 | 98.5 |
| TiO$_2$ Filler (SCC 11692) | 1.5 |
| Total | 100 |
| 10 wt. % Skin Layers | |
| (2 Layers at 5 wt. % Each) | |
| LLDPE (DOWLEX ™ 2517) | 59 |
| LLDPE (DOWLEX ™ 2047) | 39.5 |
| TiO$_2$ Filler (SCC 11692) | 1.5 |
| Total | 100 |

Example 3

A film containing 90 wt % of a core layer and two 5 wt. % skin layers was extruded. The film had a basis weight of 60 gsm, and the components are shown below in Table 3.

TABLE 3

|  | Wt. % |
| --- | --- |
| 90 wt. % core layer | |
| VISTAMAXX ™ 6102 | 50 |
| SEBS (KRATON ™ MD 6937) | 45 |
| TiO$_2$ Filler (SCC 11692) | 5 |
| Total | 100 |
| 10 wt. % Skin Layers | |
| (2 Layers at 5 wt. % Each) | |
| LLDPE (DOWLEX ™ 2517) | 59 |
| LLDPE (DOWLEX ™ 2047) | 39.5 |
| TiO$_2$ Filler (SCC 11692) | 1.5 |
| Total | 100 |

Example 4

The ability to form a spunbond nonwoven facing was demonstrated. The spunbond nonwoven facing had a basis weight of about 17 gsm and included 69 wt % ASPUN™ 6850 A linear low density polyethylene (LLDPE) (Dow Chemical Company of Midland, Mich.), 29 wt. % of INFUSE™ 9817 elastomeric copolymer of polyethylene (Dow Chemical Company of Midland Mich.), and 2 wt. % of titanium dioxide filler. The spunbond nonwoven facing was bonded by passing the facing through two rolls, where one roll was heated to a temperature of 250° F. (121° C.) and the other roll was heated to a temperature of 230° F. (110° C.).

Example 5

The ability to form a spunbond nonwoven facing was demonstrated. The spunbond nonwoven facing had a basis weight of about 17 gsm and included 69 wt. % ASPUN™ 6850A linear low density polyethylene (LLDPE) (Dow Chemical Company of Midland, Mich.), 29 wt. % of INFUSE™ 9817 elastomeric copolymer of polyethylene (Dow Chemical Company of Midland Mich.), and 2 wt. % of titanium dioxide filler. The spunbond nonwoven facing was bonded by passing the facing through two rolls, where the pressure exerted by the rolls at the nip was 290 psi, and where both rolls were heated to a temperature of 250° F. (121° C.).

Example 6

The ability to form a spunbond nonwoven facing was demonstrated. The spunbond nonwoven facing had a basis weight of about 17 gsm and included 69 wt. % DOWLEX™ 2517 linear low density polyethylene (LLDPE) (Dow Chemical Company of Midland, Mich.), 29 wt. % of INFUSE™ 9817 elastomeric copolymer of polyethylene (Dow Chemical Company of Midland Mich.), and 2 wt. % of titanium dioxide filler. During bonding, the laminate stuck to the bonder.

Example 7

The ability to form a spunbond nonwoven facing was demonstrated. The spunbond nonwoven facing had a basis weight of about 17 gsm and included 98 wt. % DOWLEX™ 2517 linear low density polyethylene (LLDPE) (Dow Chemical Company of Midland, Mich.) and 2 wt. % of titanium dioxide filler. The nonwoven facing was poorly formed.

Example 8

The ability to form a spunbond nonwoven facing was demonstrated. The spunbond nonwoven facing had a basis weight of about 15 gsm and included 99 wt. % ASPUN™ 6850 A linear low density polyethylene (LLDPE) (Dow Chemical Company of Midland, Mich.) and 1 wt. % of titanium dioxide filler. The spunbond nonwoven facing was bonded by passing the facing through two rolls, where the pressure exerted by the rolls at the nip was 290 psi, and where both rolls were heated to a temperature of 290° F. (143° C.).

Example 9

The ability to form a spunbond nonwoven facing was demonstrated. The spunbond nonwoven facing had a basis weight of about 15 gsm and included 99 wt. % DOW™ 61800 linear low density polyethylene (LLDPE) (Dow Chemical Company of Midland, Mich.) and 1 wt. % of titanium dioxide filler.

Example 10

The ability to form a spunbond nonwoven facing was demonstrated. The spunbond nonwoven facing had a basis weight of about 15 gsm and included 89 wt. % DOW™ 61800 linear low density polyethylene (Dow Chemical Company of Midland, Mich.) 10 wt. % of INFUSE™ 9817 elastomeric copolymer of polyethylene (Dow Chemical Company of Midland Mich.), and 1 wt. % of titanium dioxide filler. The spunbond nonwoven facing was bonded by passing the facing through two rolls, where both rolls were heated to a temperature of 270° F. (132° C.).

Example 11

The ability to form a spunbond nonwoven facing was demonstrated. The spunbond nonwoven facing had a basis weight of about 15 gsm and included 69 wt. % ASPUN™ 6850A linear low density polyethylene (Dow Chemical Company of Midland, Mich.), 30 wt. % of INFUSE™ 9817 elastomeric copolymer of polyethylene (Dow Chemical Company of Midland Mich.), and 1 wt. % of titanium dioxide filler.

Example 12

The ability to form a spunbond nonwoven facing was demonstrated. The spunbond nonwoven facing had a basis weight of about 15 gsm and included 69 wt. % ASPUN™ 6850A linear low density polyethylene (Dow Chemical Company of Midland, Mich.), 30 wt. % of AFFINITY™ EG 8185 polyethylene-based plastomer (Dow Chemical Company of Midland Mich.), and 1 wt. % of titanium dioxide filler.

Example 13

Laminates were formed containing the film of Example 1 disposed between two nonwoven facings. The first nonwoven facing was a spunbond facing formed as described in Example 4 and having a basis weight of 17 gsm. The second nonwoven facing was a bonded carded web having a basis weight of 18 gsm and commercially available from Sandler AG of Germany.

To form the laminate, the film of Example 1 was extrusion cast onto a chill roll at 76° F. The film was then e-beam crosslinked at 150 keV and 150 kGy. The film was then laminated on one side to the spunbond facing of Example 4 and on the other side to the bonded carded web facing via a pneumatic nip section via BOSTIK™ H2494 adhesive. The pneumatic nip section included two rolls, where a top roll included an 80 Shore A hardness silicone rubber and the bottom roll included a steel roll with a high release coating. A round hole die with 8 holes per inch was used to apply the adhesive at 1.5 gsm add on per side. The resulting laminate was then fed into a prototype groove roll unit with 8 grooves per inch and having a peak to peak distance of 0.125 inches and a depth of 0.272 inches. The laminate was engaged at a depth range of 50% to 80% of the depth of the grooves. The groove roll unit was heated using an oil heater, and grooves were formed in the laminate to decouple the facings from the elastic film.

Next, the two facing sides of the laminate were post-bonded as described below by feeding the laminate into a developmental bonding unit which included either smooth anvil rolls or patterned rolls. The rolls were heated by oil to the desired bonding temperature (200° F. or 230° F.) and the pneumatic nip pressure was varied from 15 psi to 50 psi.

After the laminates were formed, the laminates were post-bonded using various temperatures and pressures. Tensile, hook engagement, and stress relaxation testing as defined above were performed on each of the samples 1-7 of Table 4, as shown in Tables 5-9 below.

TABLE 4

Posting-Bonding Conditions

| Sample | Bond Pressure (psi) | Bond Temperature (° F.) | Nip Speed (fpm) | Bond Pattern |
|---|---|---|---|---|
| 1 | 15 | 200 | 20 | Smooth Roll |
| 2 | 25 | 200 | 20 | Smooth Roll |
| 3 | 40 | 200 | 20 | Smooth Roll |

TABLE 4-continued

Posting-Bonding Conditions

| Sample | Bond Pressure (psi) | Bond Temperature (° F.) | Nip Speed (fpm) | Bond Pattern |
|---|---|---|---|---|
| 4 | 20 | 200 | 20 | Smooth Roll |
| 5 | 30 | 230 | 30 | Wire Weave |
| 6 | 40 | 230 | 30 | Wire Weave |
| 7 | 40 | 230 | 30 | Wire Weave |

TABLE 5

Hook Engagement: Anvil on Anvil (Smooth)

| | | Spun Bond Side | | Bonded Carded Web Side | |
|---|---|---|---|---|---|
| Sample | Bond Pressure/ Temperature psi/° F. | Elongation (%) | Load at Failure (grams-force) | Elongation (%) | Load at Failure (grams-force) |
| 8 | 15/200 | 130 | 1415 | 67 | 680 |
| 9 | 25/200 | 120 | 1470 | 49 | 565 |
| 10 | 30/200 | 160 | 1945 | 60 | 630 |
| 11 | 40/200 | 80 | 1400 | 70 | 740 |
| 12 | 30/230 | 60 | 650 | 90 | 1270 |
| 13 | 40/230 | 70 | 920 | 120 | 1610 |

As shown above in Samples 8-13, it is noted that a higher elongation at break and a higher load at failure can be achieved when post bonding was carried out at lower temperatures and pressures on the spunbond side of the laminate, while the opposite was true for the bonded carded web side of the laminate.

TABLE 6

Hook Engagement: Anvil on Wire Weave

| | | Spun Bond Side | | Bonded Carded Web Side | |
|---|---|---|---|---|---|
| Sample | Bond Pressure/ Temperature psi/° F. | Elongation (%) | Load at Failure (grams-force) | Elongation (%) | Load at Failure (grams-force) |
| 14 | 20/200 | 75 | 890 | 110 | 1375 |
| 15 | 30/230 | 60 | 650 | 49 | 565 |
| 16 | 40/230 | 70 | 920 | 120 | 610 |

As shown above in Samples 14-16, it is noted that a higher elongation at break could be achieved when post bonding was carried out at lower temperatures and pressures on the spunbond side of the laminate, while the opposite was true for the bonded carded web side of the laminate.

TABLE 7

Tensile Properties: Anvil on Anvil Post-Bonded Laminates Spun Bond Side

| Sample | Bond Pressure/ Temperature psi/° F. | Elongation (%) | Load at Failure (grams-force) |
|---|---|---|---|
| 17 | N/A (Control) | >800* | >4500* |
| 18 | 15/200 | >800* | >4500* |
| 19 | 25/200 | >800* | >4500* |
| 20 | 30/200 | >800* | >4500* |
| 21 | 40/200 | 800 | 4000 |

*Indicates sample reached the displacement limit of the MTS tensile test frame

As shown above in Samples 18-21, bonding the spunbond side of the laminate at 200° F. and at pressures ranging from 15 psi to 40 psi with smooth rollers did not negatively impact the tensile properties of the laminate as compared to the unbonded control Sample 20, and elongations well over 200% were achieved.

TABLE 8

Tensile Properties: Anvil on Wire Weave Post-Bonded Laminates Spun Bond Side

| Sample | Bond Pressure/ Temperature psi/° F. | Elongation (%) | Load at Failure (grams-force) |
|---|---|---|---|
| 22 | 20/230 | 610 | 2750 |
| 23 | 30/230 | 690 | 3700 |
| 24 | 40/230 | 640 | 3200 |

As shown above in Samples 22-24, bonding the spunbond side of the laminate at 230° F. and at pressures ranging from 20 psi to 40 psi with smooth rollers did slightly decrease the tensile properties of the laminate as compared to the unbonded control Sample 20, although elongations well over 200% were achieved. The decrease in the tensile properties is the result of apertures formed in the facings during post-bonding that were not present when smooth rolls were used for post-bonding.

TABLE 9

Stress Relaxation Testing: Anvil on Anvil Laminates Spun Bond Side

| Sample | Bond Pressure/ Temperature psi/° F. | Slope | Load Loss (%) |
|---|---|---|---|
| 25 | N/A (Control) | 0.09 | 48 |
| 26 | 15/200 | 0.08 | 49 |
| 27 | 25/200 | 0.07 | 43 |
| 28 | 30/200 | 0.07 | 46 |
| 29 | 40/230 | 0.09 | 52 |

A lower slope and load loss percent during stress relaxation testing is generally indicative of a material that has better elastic behavior. As shown above, Samples 26-28, which were bonded at 200° F. and at pressures ranging from 15 psi to 30 psi, maintained or had better elastic behavior than the control sample which was not post-bonded.

In summary, the laminates of the present invention exhibited elastic characteristics, while also maintaining good mechanical properties and exhibiting good hook or tab engagement.

Example 14

Figure 11:
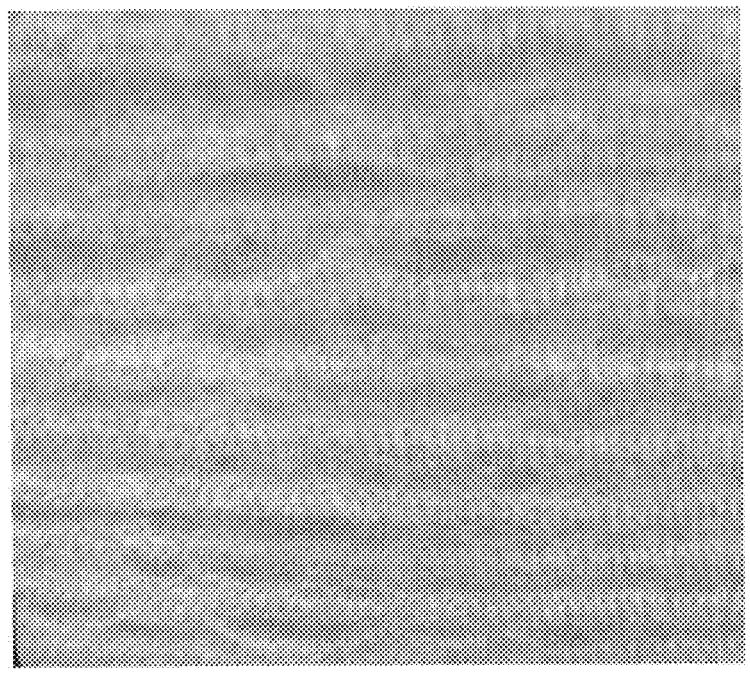
FIG. 11 is a photograph of a nonwoven facing formed in accordance with one embodiment of the present invention after post-bonding and after 70% elongation.
Figure 12:
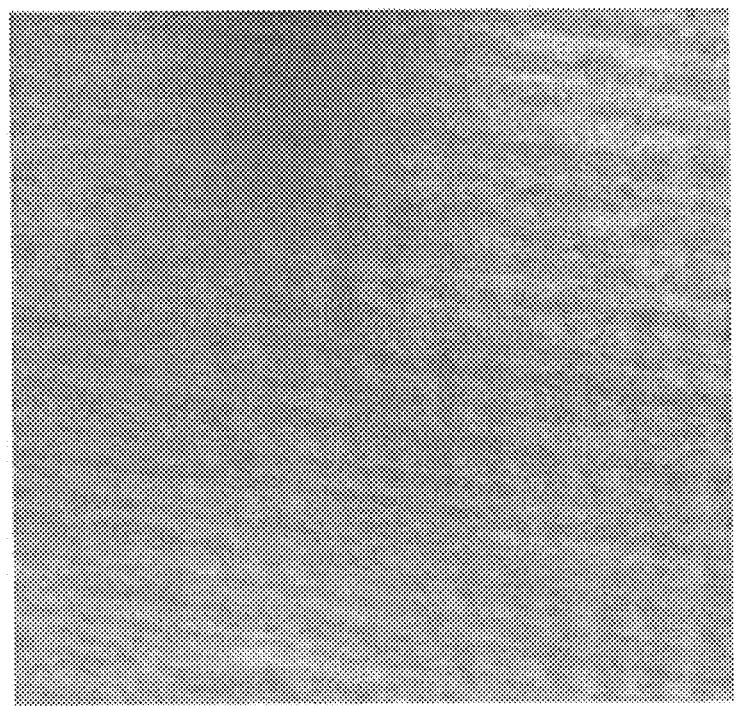
FIG. 12 is a photograph of a nonwoven facing formed in accordance with one embodiment of the present invention without post-bonding and after 70% elongation.

Next, the ability to form a laminate including the film as formed in Example 2 disposed between two 100% spunbond facings was demonstrated. FIG. 11 is a photograph of the film after it has been post-bonded with a patterned roll and stretched to 70% elongation. Meanwhile, FIG. 12 is a photograph of the laminate without any post-bonding and stretched to 70% elongation. A comparison of FIGS. 11 and 12 shows that a bond pattern is visible on the laminate of FIG. 11, which is not visible on FIG. 12.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An elastic nonwoven laminate having a machine direction and a cross-machine direction, the elastic nonwoven laminate comprising an unstretched elastic film disposed between a first nonwoven facing and a second nonwoven facing, wherein the first nonwoven facing comprises a first polyolefin, wherein the first nonwoven facing is meltblown or spunbond, wherein the first nonwoven facing and the second nonwoven facing are simultaneously grooved in the machine direction or cross-machine direction to decouple the first nonwoven facing and the second nonwoven facing from the elastic film, wherein grooves in the first nonwoven facing correspond with grooves in the second nonwoven facing, and wherein an outer surface of each of the first nonwoven facing and the second nonwoven facing is post-bonded after the first nonwoven facing and the second nonwoven facing are simultaneously grooved such that from about 1 groove per inch to about 12 grooves per inch are present on the outer surface of each of the first nonwoven facing and the second nonwoven facing after post-bonding, wherein the outer surface of each of the first nonwoven facing and the second nonwoven facing are bonded in a pattern comprising bonded areas, wherein bonded areas of the first nonwoven facing and the second nonwoven facing are non-fibrous, wherein the elastic nonwoven laminate has a percent elongation of at least about 200% in the cross-machine direction, wherein the first nonwoven facing and the second nonwoven facing each exhibit reduced fiber pull-out compared to a nonwoven facing that is not post-bonded.

2. The elastic nonwoven laminate of claim 1, wherein the first polyolefin comprises polyethylene, polypropylene, or a combination thereof.

3. The elastic nonwoven laminate of claim 1, wherein the first nonwoven facing further comprises a second polyolefin, wherein the second polyolefin comprises an elastomeric semi-crystalline polyolefin.

4. The elastic nonwoven laminate of claim 3 wherein the elastomeric semi-crystalline polyolefin is an ethylene/$\alpha$-olefin copolymer, propylene/$\alpha$-olefin copolymer, or a combination thereof.

5. The elastic nonwoven laminate of claim 3, wherein the first polyolefin is present in an amount ranging from about 50 wt. % to about 99 wt. % and the second polyolefin is present in an amount ranging from about 0.5 wt. % to about 60 wt %, based on the total weight of the first nonwoven facing.

6. The elastic nonwoven laminate of claim 1, wherein the elastic film comprises a core layer disposed between two skin layers, wherein the core layer is an elastic layer comprising a styrenic block copolymer, an ethylene/$\alpha$-olefin copolymer, a propylene/$\alpha$-olefin copolymer, or a combination thereof.

7. The elastic nonwoven laminate of claim 1, wherein the elastic film comprises a core layer disposed between two skin layers, wherein the core layer is a strength layer, and wherein the two skin layers are elastic layers.

8. The elastic nonwoven laminate of claim 1, further comprising a frangible layer.

9. The elastic nonwoven laminate of claim 1, wherein the elastic nonwoven laminate has a percent elongation ranging from 610% to about 1000% in the cross-machine direction.

10. The elastic nonwoven laminate of claim 1, wherein post-bonding occurs at a temperature ranging from about 175° F. to about 250° F.

* * * * *